US011685792B2

(12) United States Patent
Levy et al.

(10) Patent No.: US 11,685,792 B2
(45) Date of Patent: *Jun. 27, 2023

(54) ANTIBODIES AGAINST HUMAN CD39 AND USE THEREOF FOR INHIBITING T REGULATORY CELLS ACTIVITY

(71) Applicant: INSERM (Institut National de la Sante et de la Recherché Medicale), Paris (FR)

(72) Inventors: Yves Levy, Creteil (FR); Jean-Francois Eliaou, Creteil (FR); Armand Bensussan, Creteil (FR); Nathalie Bonnefoy-Berard, Creteil (FR)

(73) Assignee: INSERM (Institut National de la Sante et de la Recherche Medicale), Paris (FR)

( * ) Notice: Subject to any disclaimer, the term of this patent is extended or adjusted under 35 U.S.C. 154(b) by 492 days.

This patent is subject to a terminal disclaimer.

(21) Appl. No.: 16/880,835

(22) Filed: May 21, 2020

(65) Prior Publication Data

US 2021/0032367 A1 Feb. 4, 2021

Related U.S. Application Data

(60) Continuation of application No. 14/939,650, filed on Nov. 12, 2015, now Pat. No. 10,662,253, which is a division of application No. 12/863,461, filed as application No. PCT/EP2009/051078 on Jan. 30, 2009, now abandoned.

(30) Foreign Application Priority Data

Jan. 31, 2008 (EP) .................................... 08300061
Aug. 20, 2008 (EP) .................................... 08162683

(51) Int. Cl.
*C07K 16/40* (2006.01)
*C07K 16/28* (2006.01)
*A61K 39/00* (2006.01)

(52) U.S. Cl.
CPC .......... *C07K 16/40* (2013.01); *C07K 16/2896* (2013.01); *A61K 2039/505* (2013.01); *C07K 2317/24* (2013.01); *C07K 2317/565* (2013.01); *C07K 2317/76* (2013.01); *Y02A 50/30* (2018.01)

(58) Field of Classification Search
None
See application file for complete search history.

(56) References Cited

U.S. PATENT DOCUMENTS

| 4,179,337 A | 12/1979 | Davis et al. |
| 4,301,144 A | 11/1981 | Iwashita et al. |
| 4,496,689 A | 1/1985 | Mitra |
| 4,640,835 A | 2/1987 | Shimizu et al. |
| 4,670,417 A | 6/1987 | Iwasaki et al. |
| 4,791,192 A | 12/1988 | Nakagawa et al. |
| 4,816,567 A | 3/1989 | Cabilly et al. |
| 4,861,719 A | 8/1989 | Miller |
| 5,202,238 A | 4/1993 | Fell et al. |
| 5,204,244 A | 4/1993 | Fell et al. |
| 5,225,539 A | 7/1993 | Winter et al. |
| 5,229,275 A | 7/1993 | Goroff |
| 5,278,056 A | 1/1994 | Bank et al. |
| 5,530,101 A | 6/1996 | Queen et al. |
| 5,565,332 A | 10/1996 | Hoogenboom |
| 5,567,610 A | 10/1996 | Borrebaeck et al. |
| 5,585,089 A | 12/1996 | Queen et al. |
| 5,660,827 A | 8/1997 | Thorpe et al. |
| 5,859,205 A | 1/1999 | Adair et al. |
| 5,882,877 A | 3/1999 | Gregory et al. |
| 5,994,524 A | 11/1999 | Matsushima et al. |
| 6,013,516 A | 1/2000 | Verma et al. |
| 6,018,032 A | 1/2000 | Koike et al. |
| 6,127,175 A | 10/2000 | Vigne et al. |
| 6,162,963 A | 12/2000 | Kucherlapati et al. |
| 6,464,998 B1 | 10/2002 | Beuzard et al. |
| 6,737,056 B1 | 5/2004 | Presta |
| 8,865,653 B2 | 10/2014 | Zitvogel et al. |
| 9,605,080 B2 | 3/2017 | Lonberg et al. |
| 10,662,253 B2 | 5/2020 | Levy et al. |
| 11,377,503 B2 | 7/2022 | Chanteux et al. |
| 2005/0037382 A1 | 2/2005 | Robson et al. |
| 2005/0158280 A1 | 7/2005 | Robson et al. |
| 2006/0002932 A1 | 1/2006 | Vieweg |
| 2006/0246006 A1 | 11/2006 | Johnson et al. |
| 2009/0068202 A1 | 3/2009 | Chen et al. |
| 2010/0303828 A1 | 12/2010 | Levy et al. |

(Continued)

FOREIGN PATENT DOCUMENTS

EP 0125023 11/1984
EP 0173494 A2 3/1986

(Continued)

OTHER PUBLICATIONS

Rabia et al. 2018, Biochem. Eng. J. vol. 137: 365-374.*
Scott et al., 2012, vol. 12. Nature Reviews, pp. 278-287.*
Townsend et al., 2016, Front. Immunol. vol. 7: 1-12.*
Abe et al., "Increased_Foxp3+ CD4+ Regulatory T Cells with Intact Suppressive Activity but Altered Cellular Localization in Murine Lupus", Am. J. Path. (2008) 173(6): 1682-1692.
Allard et al., "The ectonucleotidases CD39 and CD73: novel checkpoint inhibitor targets", Immunol Rev. (Mar. 2017): 276(1):121-144.
Altschul et al., "Basic Local Alignment Search Tool", J Mol Biol. (1990) 215: 403-410.
Altschul et al., "Gapped BLAST and PSI-BLAST: a new generation of protein database search programs", Nucl Acids Res. (1997) 25(17): 3389-3402.

(Continued)

Primary Examiner — Amy E Juedes
(74) Attorney, Agent, or Firm — Knobbe, Martens, Olson & Bear, LLP

(57) ABSTRACT

The invention relates to antibodies against human CD39 and use thereof for inhibiting T regulatory cells (Treg) activity. More particularly CD39 antibodies may be used for the treatment or prevention of cancers and infectious diseases.

9 Claims, 4 Drawing Sheets

Figure 1:
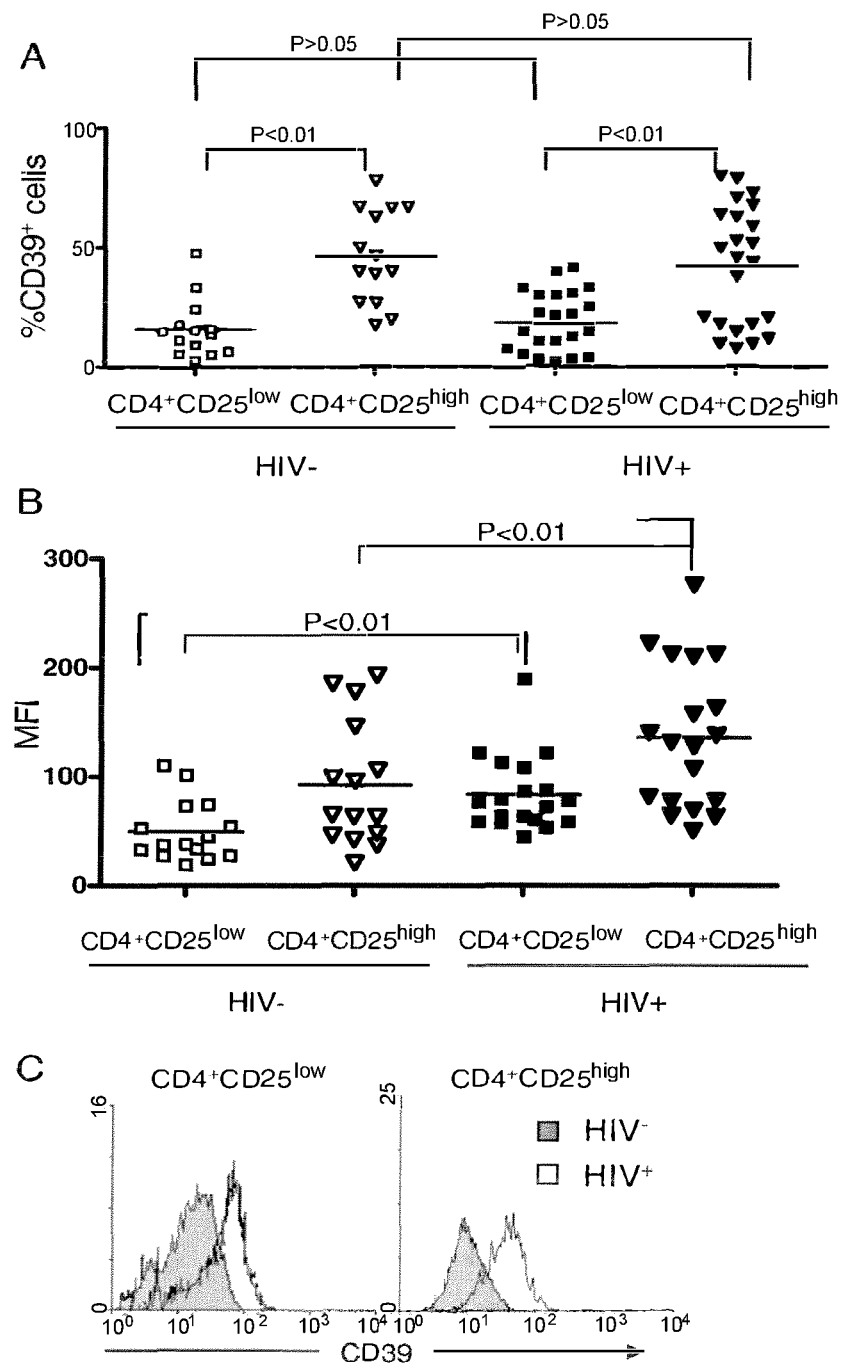

Specification includes a Sequence Listing.

(56) References Cited

U.S. PATENT DOCUMENTS

| | | |
|---|---|---|
| 2013/0034559 A1 | 2/2013 | Queva et al. |
| 2013/0273062 A1 | 10/2013 | Bensussan et al. |
| 2016/0137747 A1 | 5/2016 | Levy et al. |
| 2019/0062448 A1 | 2/2019 | Soros et al. |
| 2019/0153113 A1 | 5/2019 | Bastid et al. |
| 2019/0218304 A1 | 7/2019 | Chanteux et al. |
| 2019/0218308 A1 | 7/2019 | Chanteux et al. |
| 2019/0389961 A1 | 12/2019 | Chanteux et al. |
| 2020/0024357 A1 | 1/2020 | Chanteux et al. |
| 2021/0261686 A1 | 8/2021 | Bensussan et al. |

FOREIGN PATENT DOCUMENTS

| | | |
|---|---|---|
| EP | 0239400 | 9/1987 |
| EP | 0519596 A1 | 12/1992 |
| EP | 0592106 A1 | 4/1994 |
| WO | WO 1987/002671 | 5/1987 |
| WO | WO 1987/005330 | 9/1987 |
| WO | WO 1991/009967 | 7/1991 |
| WO | WO 1994/019478 | 9/1994 |
| WO | WO 1995/014785 | 6/1995 |
| WO | WO 1996/002576 | 2/1996 |
| WO | WO 1996/022378 | 7/1996 |
| WO | WO 1997/010354 | 3/1997 |
| WO | WO 1998/045322 | 10/1998 |
| WO | WO 1999/058572 | 11/1999 |
| WO | WO 2003/052121 | 6/2003 |
| WO | WO 2003/101485 | 12/2003 |
| WO | WO 2006/111986 | 10/2006 |
| WO | WO 2006/121168 | 11/2006 |
| WO | WO 2007/005874 | 1/2007 |
| WO | WO 2009/014708 | 1/2009 |
| WO | WO 2009/095478 | 8/2009 |
| WO | WO 2009/101611 | 8/2009 |
| WO | WO 2009/114335 | 9/2009 |
| WO | WO 2010/077634 | 7/2010 |
| WO | WO 2011/066389 | 6/2011 |
| WO | WO 2011/066501 | 6/2011 |
| WO | WO 2012/065950 | 5/2012 |
| WO | WO 2012/085132 | 6/2012 |
| WO | WO 2012/087746 | 6/2012 |
| WO | WO 2012/145493 | 10/2012 |

OTHER PUBLICATIONS

Amersham Biosciences, "Antibody Purification—Handbook", Publication No. 18-1037-46, Edition AC, (2002) 112 pages.

Bastid et al., "ENTPD1/CD39 is a promising therapeutic target in oncology", Oncogene (2013) 32(14):1743-1751 [publ online Jul. 2, 2012].

Bastid et al., "Inhibition of CD39 enzymatic function at the surface of tumor cells alleviates their immunosuppressive activity", Cancer Imunol Res. (Nov. 2014) 3(3):254-265.

Baudino et al., "Crucial role of aspartic acid at Position 265 in the CH2 Domain for Murnie IgG2a and IgG2b Fc-associated Effector Functions", J Immunol. (2008) 181: 6664-6669.

Beavis et al., "CD73: a potent suppressor of antitumor immune responses", Trends in Immunol. (2012) 33(5): 231-237.

Benussan et al., "Detection of membrane-bound HLA-G translated products with a specific monoclonal antibody", PNAS U.S.A., 1995, 92: 10292-10296.

Bluestone et al., "Natural versus adaptive regulatory T cells", Nat Rev Immunol. (2003) 3(3):253-257.

Bonnefoy et al., "CD39: A complementary target to immune checkpoints to counteract tumor-mediated immosuppression", Oncoimmunology. (2015) 4(5):e1003015.

Borsellino et al., "Expression of ectonucleotidase CD39 by Foxp3+ Treg cells: hydrolysis of extracellular ATP and immune suppression", (Aug. 2007) 110(4): 1225-1232.

Brady et al., "New Cosmid Vectors Developed for Eukaryotic DNA Cloning", Gene (1984) 27(2):223-232.

Bruhns, "Properties of mouse and human IgG receptors and their contribution to disease models," Blood, Jun. 2012, 119(24):5640-5649.

Buffon et al., "NTPDase and 5' ecto-nucleotidase expression profiles and the pattern of extracellular ATP metabolism in the Walker 256 tumor", Biochim Biophys Acta. (2007) 1770(8):1259-1265.

Burgers et al., "The challenges of HIV vaccine development", Best Pract Res Clin OBst Gyn. (2005) 19(2): 277-291.

Cabrera et al., "An Immunomodulatory Role for CD4+CD25+ Regulatory T Lymphocytes in Hepatitis C Virus Infection", Hepatol. (2004) 40(5): 1062-1071.

Caron et al., "Engineered humanized dimeric forms of IgG are more effective antibodies", J Exp Med. (1992) 176(4):1191-1195.

Carrillo et al., "The Multiple Sequence Alignment Problem in Biology", Siam J Appl Math. (1988) 48(5): 1073-1082.

Carter et al., "Humanization of an anti-p185HER2 antibody for human cancer therapy", PNAS U.S.A. (1992) 89: 4285-4289.

Chardés et al., "Efficient amplification and direct sequencing of mouse variable regions from any immunoglobulin gene family", FEBS Lett. (1999) 452(3):386-394.

Chiappelli et al., "Neuroendocrine immunity in patients with Alzheimer's disease: toward translational epigenetics", Bioinformation (2007) vol. 2: 1-4.

Chothia et al., "Canonical Structures for the Hypervariable Regions of Immunoglobulins", J Mol Biol. (1987) 196: 901-917.

Clackson et al., "A Hot Spot of Binding Energy in a Hormone-Receptor Interface", Science (1995) 267: 383-386.

Clayton et al., "Cancer Exosomes Express CD39 and CD73, which suppress T Cells through Adenosine Production", J Immunol. (Jul. 2011) 187(2):676-683.

Cole et al., "The EBV-Hybridoma Technique and its Application in Human Lung Cancer" in *Monoclonal Antibodies and Cancer Therapy* Reisfeld et al. [Eds.] (1985) pp. 77-96.

Coligan et al. [Eds.], "Current Protocols in Immunology", John Wiley & Sons, Inc. (1991); TOC.

Connolly et al., "Female Mice Chimeric for Expression of the Simian Virus 40 Tag under Control of the MISIIR Promoter Develop Epithelial Ovarian Cancer", Cancer Res. (2003) 64(6):1389-1397.

Cote et al., "Generation of human monoclonal antibodies reactive with cellular antigens", Proc Natl Acad Sci USA (1983) 80:2026-2030.

Damle et al., "B-cell chronic lymphocytic leukemia cells express a surface membrane phenotype of activated, antigen-experienced B lymphocytes", Blood (2002) 99(11): 4087-4093.

Deaglio et al., "Adenosine generation catalyzed by CD39 and CD73 expressed on regulatory T cells mediates immune suppression", J Exp Med., (2007) 204(6):1257-1265.

Devereux et al., "A comprehensive set of sequence analysis programs for the VAX", Nucl Acid Res. (1984) 12(1): 387-395.

Downard K.M., "Contributions of mass spectrometry to structural immunology", J Mass Spectrom. (2000) 35: 493-503.

Drosopoulos et al., Site-directed mutagenesis of human endothelial cell ecto-ADPase/soluble CD39: requirement of glutamate 174 and serine 218 for enzyme activity and inhibition of platelet recruitment. Biochemistry (2000) 39(23):6936-6943.

Dwyer et al., "CD39 and control of cellular immune responses", Purinergic Signal. (2007) 3(1-2):171-180.

Dwyer et al., "Expression of CD39 by Human Peripheral Blood CD$+CD25+ T Cells Denotes a Regulatory Memory Phenotype", Am J Transplantation (2010) 10: 2410-2420.

Dzhandzhugazyan et al., "Ecto-ATP diphosphohydrolase/CD39 is overexpressed in differentiated human melanomas", FEBS Lett. (1998) 430:227-230.

Edge et al., "Deglycosylation of glycoproteins by trifluoromethanesulfonic acid", Anal Biochem. (1981) 118(1):131-137.

Ehring H., "Hydrogen Exchange/Electrospray Ionization Mass Spectrometry Studies of Structural Features of Proteins and Protein/Protein Interactions", Analyt Biochem. (1999) 267: 251-259.

Engen et al, "Metrohm 792 Basic IC", Anal Chem. (2001) 73: 256A-265A.

(56) References Cited

OTHER PUBLICATIONS

Erdmann et al., "Activation of Th1 and Tc1 cell adenosine A2A receptors directly inhibits IL-2 secretion in vitro and IL-2-driven expansion in vivo", Blood (Jun. 2005) 105(12): 4707-4714.

European Journal Of Immunology, Instructions to Authors, 2010, in 6 pages.

Fägerstam et al., "Detection of Antigen-Antibody Interactions by Surface Plasmon Resonance", J Mol Recogn. (1990) 3(5/6): 208-214.

Fredholm et al., "Adenosine, an endogenous distress signal, modulates tissue damage and repair", Cell Death Differ. (2007) 14(7):1315-1323.

Fujarewicz et al., "A multi-gene approach to differentiate papillary thyroid carcinoma from benign lesions: gene selection using support vector machines with bootstrapping," Endocr Relat Cancer. (2007) 14(3):809-826.

Gavilondo et al., "Antibody Engineering at the Millennium", BioTechniques (Jul. 2000) 29:128-145.

Gazzano-Santoro et al., "A non-radioactive complement-dependent cytotoxicity array for anti-CD20 monoclonal antibody", J Immunol Methods (1997) 202(2):163-171.

Genbank Accession No. P49961; "Ectonucleoside triphosphate diphosphohydrolase 1 . . . ", Created: Oct. 1, 1996; 7 pages.

Genbank Accession No. NP_001237; "Ectonucleoside triphosphate diphosphohydrolase 2 Isofpr, 2 [*Homo sapiens*]", Created: Jul. 2008; 3 pages.

Genbank Accession No. NP_001238; "Ectonucleoside triphosphate diphosphohydrolase 2 Isoform 1 [*Homo sapiens*]", Created: Dec. 2015; 3 pages.

Genbank Accession No. NP_001239.2; "Ectonucleoside triphosphate diphosphohydrolase 2 Isoform 1 [*Homo sapiens*]", Created: May 2014; 3 pages.

Genbank Accession No. NP_001240.1; "Ectonucleoside triphosphate diphosphohydrolase 5 Isoform 1 Precursor [*Homo sapiens*]", Created: Jan. 2009; 3 pages.

Genbank Accession No. U64863.1; "Human hPD-1 (hPD-1) mRNA, complete cds", Created: Oct. 12, 2005; 3 pages.

Gerber et al., "Pharmacology and Pharmacodynamics of Bevacizumab as Monotherapy or in combination with Cytotoxic Therapy in Preclinical Studies", Cancer Res. 2005; 65(3):671-680.

Gillies et al., "A tissue-specific transcription enhancer element is located in the major intron of a rearranged immunoglobulin heavy chain gene", Cell (1983) 33(3):717-728.

Goding J.W., "Monoclonal Antibodies: Principles and Practice", 2nd Edition, Academic Press/Harcourt Brace Javanovich, Publishers (1986); Chapter 3, 47 pages.

Goede et al., "Induction of Inflammatory Angiogenesis by Monocyte Chemoattractant Protein-1", Int. J. Canc.(1999) 82: 765-770.

Gouttefangeas et al., "The CD29 molecule defines distinct cytotoxic subsets within alloactivated human CD8-positive cells", Eur J Immunol. 1992, 22:2681-2685.

Gouttefangeas et al., "Biochemical analysis and epitope mapping of mAb defining CD39"; in Schlossman, et al. [Eds.] *Leucocyte Typing V*. Oxford University Press, New York, 1995; pp. 383-385.

Green et al., "Antigen-specific human monoclonal antibodies from mice engineered with human Ig heavy and light chain YACs", Nature Genet. (1994) 7: 13-21.

Gribskov et al. [Eds.], "Sequence Analysis Primer", M Stockton Press (1991); TOC.

Griffin et al. [Eds.], "Computer Analysis of Sequence Data—Part I" in *Methods in Molecular Biology* Humana Press (1994); TOC.

Gu et al., "Human CD39hi regulatory T cells present stronger stability and function under inflammatory conditions", Cell Mol Immunol. (2017) 14: 521-528; publ. online Jul. 4, 2016.

Harlow et al. [Eds.] "Antibodies—A Laboratory Manual", Cold Spring Harbor Laboratory (1988); TOC.

Häusler et al., "CD39 is expressed by human ovarian carcinoma cell lines and inhibits immunological tumour defence", Presentation at the University Women's Hospital Würzburg, Germany; Obstetrics Gynaecology (2008) 68—PO—DOI: 10.1055/s-0028-1089305; Original in German; English Translations in 4 pages.

Häusler et al., "CD39 wird in vivo und in vitro von Ovarialkarzinomzellen experimiert und inhibiert die lytische Aktivität von NK Zellen", Geburtshilfe Frauenheilkd. (2009), 69—P106; DOI: 10.1055/s-0029-1225180; Abstract in 1 page.

Häusler et al., "Ovarian carcinoma cells suppress anti-tumoral immune responses by extracellular generation of adenosine via CD39 and CD73", Geburshilfe Frauenheilkd. (2009) 69—A042; DOI: 10.1055/s-0029-1238961; Original in German (Two Engl. Translations) in 5 pages.

Häusler et al., "Ectonucleotidases CD39 and CD73 on OvCA cells are potent adenosine-generating enzymes responsible for adenosine receptor 2A-dependent suppression of T cell function and NK cell cytotoxicity", Cancer Immunol Immunother. (2011) 60(10):1405-1418.

Häusler et al., "Anti-CD39 and anti-CD73 antibodies A1 and 7G2 improve targeted therapy in ovarian cancer by blocking adenosine-dependent immune evasion," American Journal of Translational Research, Jan. 2014, 6(2):129-139.

Hayes et al., "CD39 is a promising therapeutic antibody target for the treatment of soft tissue sarcoma", Am J Transl Res. (2015) 7(6): 1181-1188.

Hisaeda, H. "Regulatory T-cells in Infection Immunity" Experimental Med. (2007) 25(18): 2862-2867.

Hoskin et al., "Inhibition of T cell and natural killer cell function by adenosine and its contribution to immune evasion by tumor cells (Review)", Inter'l J Oncol. (2008) 32: 527-535.

Hou TJ., "Comparison of Multiple Comparison Methods for Identifying Differential Gene Expression in Simulated and Real Papillary Thyroid Cancer Microarray Data", Thesis, presented to the Faculty of the University of Texas School of Public Health (Aug. 2009) in 88 pages.

Huang et al., "NMR Identification of Epitopes of Lyme Disease Antigen OspA to Monoclonal Antibodies", J Mol Biol. (1998) 281(1): 61-67.

Jakobovits et al., "Germ-line transmission and expression of a human-derived yeast artificial chromosome", Nature (1993) 362: 255-258.

Jie et al., "Intratumoral regulatory T cells upregulate immunosuppressive molecules in head and neck cancer patients", (Oct. 2013) 1-7.

Jin et al., "CD73 on Tumor Cells Impairs Antitumor T-Cell Responses: A Novel Mechanism of Tumor-Induced Immune Suppression", Cancer Res. (2010) 70(6):2245-2255 and Addendum.

Jones et al., "Replacing the complementarity-determining regions in a human antibody with those from a mouse", Nature (1986) 321: 522-525.

Kabat et al., "Sequences of Proteins of Immunological Interest", 5th Ed. U.S. Department of Health and Human Services (NIH Publication No. 91-3242) (1991); TOC.

Kiselar et al., "Direct Identification of Protein Epitopes by Mass Spectrometry without immobilization of Antibody and Isolation of Antibody-Peptide Complexes", Anal Chem. (1999) 71(9): 1792-1801.

Kishore et al., "Expression of NTPDase1 and NTPDase2 in murine kidney: relevance to regulation of P2 receptor signaling", Am J Physiol Renal Physiol. (2005) 288(5):F1032-F1043.

Klimka et al., "Human anti-CD30 recombinant antibodies by guided phage antibody selection using cell panning", British J Cancer. (2000) 83(2): 252-260.

Knapp et al., "Crystal structure of the human ecto-5'-nucleotidase (CD73): insights into the regulation of purinergic signaling". Structure (2012) 20(12): 2161-2173.

Köhler et al., "Continuous cultures of fused cells secreting antibody of predefined specificity", Nature (1975) 256(5517):495-497.

Kondo et al., "Expression of CD73 and its ecto-5'-nucleotidase activity are elevated in papillary thyroid carcinomas", Histopathology (2006) 48(5):612-614.

Kröger et al., "Epitope-mapping of transglutaminase with parallel label-free optical detection", Biosens Bioelectr. (2002) 17: 937-944.

(56) References Cited

OTHER PUBLICATIONS

Künzli et a., "Upregulation of CD39/NTPDases and P2 receptors in human pancreatic disease", Am J Physiol Gastrointest Liver Physiol. (2007) 292(1):G223-230.

Kuwana et al., "Expression of Chimeric Receptor composed of Immunoglobulin-derived V regions and T-cell receptor-derived C regions", Biochem Biophys Res Commun. (1987) 149(3):960-968.

Leipert et al., "Investigation of the Molecular Recognition of Amino Acids by Cyclopeptides with Reflectometric Interference Spectroscopy", Angew Chem Int Ed. (1998) 37(23): 3308-3311.

Lesk A. [Ed], "Computational Molecular Biology—Sources and Methods for Sequence Analysis", Oxford University Press (1988); TOC.

Liyanage et al., "Prevalence of Regulatory T Cells is Increased in Periperal Blood and Tumor Microenvironment of Patients with Pancreas or Breast Adenocarcinoma", J Immunol. (2002) 169(5): 2756-2761.

Lonberg et al., "Antigen-specific human antibodies from mice comprising four distinct genetic modifications", Nature. (1994) 368: 856-859.

Maliszewski et al. "The CD39 lymphoid cell activation antigen—Molecular Cloning and Structural Characterization", J Immunol. (1994) 153(8):3574-3583.

Mandapathil et al., "Increased Ectonucleotidase Expression and Activity in Regulatory T Cells of patients with head and neck cancer", Clin Cancer Res. (2009) 15(20):6348-6357.

Mandapathil et al., "Targeting human inducible regulatory T cells (Tr1) in patients with cancer: blocking of adenosine-prostaglandin E2 cooperation", Expert Opin Biol Ther. (2011) 11(9):1203-1214.

Mariuzza et al., "The Structural Basis of Antigen-Antibody Recognition", Ann Rev Biophys Biophys Chem. (1987) 16:139-159.

Marshak-Rothstein et al., "Hybridoma proteins expressing the predominant idiotype of the antiazophenylarsonate response of A/J mice", PNAS (1980) 77(2): 1120-1124.

Mason et al., "Transcription cell type specificity is conferred by an immunoglobulin VH gene promoter that includes a functional consensus sequence", Cell (1985) 41(2):479-487.

Mazzanti et al., "Liver angiogenesis as a risk factor for hepatocellular carcinoma development in hepatitis C virus cirrhotic patients", World J. Gastroenterol. (2007) 13(37): 5009-5014.

McCafferty et al., "Phage antibodies: filamentous phage displaying antibody variable domains", Nature. (1990) 348: 552-554.

Meyer et al., "Saturation Transfer Difference NMR Spectroscopy for Identifying Ligand Epitopes and Binding Specificities", E. Schering Res Found Workshop 44; in *Leucocyte Trafficking;* Springer Verlag (2004) pp. 149-167.

Meyer et al., "Expression of CD39 and CD73 as means of evading anti-tumor immune responses in lung cancer", J Immunol. (Apr. 2010) 184:100.7 (Abstract).

Michaud et al., "Autophagy-dependent anticancer immune responses induced by chemotherapeutic agents in mice", Science (2011) 334(6062):1573-1577.

Miyaji et al., "Expression of human beta-interferon in Namalwa KJM-1 which was adapted to serum-free medium", Cytotech. (1990) 3(2):133-140.

Mizukami et al., "Binding region for human immunodeficiency virus (HIV) and epitopes for HIV-blocking monoclonal antibodies of the CD4 molecule defined by site-directed mutagenesis", Proc Natl Acad Sci. USA (1988) 85:9273-9277.

Mizukami et al., "A new SV40-based vector developed for cDNA expression in animal cells", J Biochem (Tokyo) (1987) 101(5):1307-1310.

Mizumoto et al., CD39 is the dominant Langerhans cell-associated ecto-NTPDase: modulatory roles in inflammation and immune responsiveness. Nat Med. (2002) 8(4):358-365.

Möller et al., "Monitoring the expression of purinoceptors and nucleotide-metabolizing ecto-enzymes with antibodies directed against proteins in native conformation", Purinergic Signalling, 3(4):359-366 (2007).

Mor et al., "Identification of Aldolase as a Target Antigen in Alzheimer's Disease", J Immunol. (2005) 175: 3439-3445.

Morrison et al., "Chimeric human antibody molecules: Mouse antigen-binding domains with human constant region domains", Proc Natl Acad Sci USA (1984) 81:6851-6855.

Müller R., "Determination of Affinity and Specificity of Anti-Hapten Antibodies by Competitive Radioimmunoassay", Meth Enzymol. (1983) 92: 589-601.

Munkonda et al., "Characterization of a monoclonal antibody as the first specific inhibitor of human NTP diphosphohydrolase-3—Partial characterization of the inhibitory epitope and potential applications", FEBS J. (2009) 276: 479-496.

Neuberger et al., "Recombinant antibodies possessing novel effector functions", Nature (1984) 312:604-608.

Nice et al., "Mapping of the antibody- and receptor-binding domains of granulocyte colongy-stimulating factor using an optical biosensor", J Chromatogr. (1993) 646: 159-168.

Nikolova et al., "CD39/Adenosine Pathway is involved in AIDS Progression", Plos Pathog. (2011) 7(7): e1002110; 14 pages.

O'Hare K. et al., "Transformation of mouse fibroblasts to methotrexate resistance by a recombinant plasmid expressing a prokaryotic dihydrofolate reductase", Proc Natl Acad Sci. USA (1981) 78(3):1527-1531.

Ohta et al., "A2A adenosine receptor protects tumors from antitumor T cells", PNAS U S A. (2006) 103(35):13132-13137.

Padlan, E.A., "A Possible Procedure for Reducing the Immunogenicity of Antibody Variable Domains while Preserving their Ligand-binding Properties", Mol Immunol (1991) 28(4/5):489-498.

Perrot et al., "Abstract 2718: Preclinical development of humanized CD39 and CD73 (IPH53) blocking antibodies targeting the ATP/adenosine immune checkpoint pathway for cancer immunotherapy", AACR Annual Meeting 2018, (Jul. 2018); DOI: 10.1158/1538-7445. AM2018-2718 in 2 pages.

Perrot et al., Preclinical development of humanized CD39 (IPH52) and CD73 (IPH53) blocking antibodies targeting the ATP/Adenosine immune checkpoint pathway for cancer immunotherapy. AACR 2018 Innate Pharma, Retrieved from the Internet: URL: https://www.innate-pharma.com/sites/default/files/poster_cd39_cd73_bat.pdf. Poster; 1 page.

Perry et al., "Increased CD39 expression on CD4+ T lymphocytes has clinical and prognostic significance in chronic lymphocytic leukemia", Ann Hematol. (2012) 91: 1271-1279.

Plückthun et al., "Mono- and Bivalent Antibody Fragments Produced in *Escherichia coli*: Engineering, Folding and Antigen Binding", Immunol Rev. (1992) 130: 151-188.

PNAS U.S.A., Information for Authors, Jan. 2013 in 5 pages.

Presta et al., "Antibody engineering", Curr Opin Struct Biol. (1992) 2: 593-596.

Presta et al., "Humanization of an Antibody Directed Against IgE", J Immunol. (1993) 151(5): 2623-2632.

Pulte et al., "CD39 activity correlates with stage and inhibits platelet reactivity in chronic lymphocytic leukemia", J Transl Med. (2007) 4:5-23.

Rawstron et al., "Chronic Lymphocytic Leukaemia (CLL) and CLL-Type Monoclonal B-Cell Lymphocytosis (MBL) Show Differential Expression of Molecules Involved in Lymphoid Tissue Homing", Cytometry B Clin Cytom. (2010) 78B(Suppl 1):S42-S46.

Remington J.R. *The Science and Practice of Pharmacy,* The Philadelphia College of Pharmacy and Science; 19th Edition (1995), TOC.

Riechmann et al., "Reshaping human antibodies for therapy", Nature (1988) 332:323-327.

Robson et al., "The E-NTPDase family of ectonucleotidases: Structure function relationships and pathophysiological significance", Purinergic Signal. (2006) 2(2):409-430.

Roguska et al., "Humanization of Murine Monoclonal Antibodies through Variable Domain Resurfacing", Proc Natl Acad Sci USA (1994) 91:969-973.

Ryan et al., "Preclinical Safety Evaluation of rhuMAbVEGF, an Antiangiogenic Humanized Monoclonal Antibody", Toxicol Pathol. (1999) 27(1): 78-86.

Saito et al., "Nuclear Magnetic Resonance Spectroscopy for the Study of B-Cell Epitopes", Methods. (1996) 9(3): 516-524.

(56) References Cited

OTHER PUBLICATIONS

Saunal et al., "Mapping of viral conformational epitopes using biosensor measurements" J Immunol Meth. (1995) 183: 33-41.
Schenk et al., "Monoclonal antibodies to rat Na+, K+-ATPase block enzymatic activity", Proc Natl Acad Sci. USA (1983) 80: 5281-5285.
Schetinger et al., "NTPDase and 5'-nucleotidase activities in physiological and disease conditions: new perspectives for human health", Biofactors. (2007) 31(2):77-98.
Schuetz et al., "Molecular Classification of Renal Tumors by Gene Expression Profiling", J Mol Diagnost. (2005) 7(2):206-218.
Shevach et al., "The lifestyle of naturally occurring CD4+ CD25+ Foxp3+ regulatory T cells", Immunol Rev. (2006) 212:60-73.
Shi et al., "Prevalence of the Mercurial-Sensitive ExtoATPase in Human Small Cell Lung Carcinoma: characterization and partial purification", Arch Biochem Biophys. (1994) 315(1):177-184.
Shitara et al., A new vector for the high level expression of chimeric antibodies in myeloma cells J Immunol Meth. (1994) 167(1-2):271-278.
Shopes B., A genetically engineered human IgG mutant with enhanced cytoloytic activity, J Immunol. (1992) 148(9):2918-2922.
Sims et al., "A Humanized CD18 Antibody Can Block Function without Cell Destruction", J Imunol. (1993) 151(4): 2296-2308.
Sitkovsky et al., "Adenosine A2A receptor antagonists: blockade of adenosinergic effects and T regulatory cells", Br J Pharmacol. (2008) 153(Suppl 1):S457-S464.
Skerra A. "Bacterial expression of immunoglobulin fragments", Curr Opin Immunol. (1993) 5: 256-262.
Smith D.W. [Ed.], "Biocomputing - Informatics and Genome Projects", Academic Press, Inc. (1994); TOC.
Sojar et al., "A chemical method for the deglycosylation of proteins", Arch Biochem Biophys. (1987) 259(1):52-57.
Stagg et al., "Extracellular adenosine triphosphate and adenosine in cancer", Ongogene (2010) 29:5346-5358.
Strohal et al., "Complete variable region sequence of a nonfunctionally rearranged kappa light chain transcribed in the nonsector P3-X63-Ag8.653 myeloma cell line", Nucl Acids Res. (1987) 15(6):2771.
Strohl W.R., "Optimization of Fc-medicated effector functions of monoclonal antibodies", Curr Opin Biotechnol. (2009) 20(6): 685-691.
Studnicka et al., "Human-engineered monoclonal antibodies retain full specific binding activity by preserving non-CDR complementarity-modulating residues", Prot Engin. (1994) 7(6):805-814.
Sun et al., "CD39/ENTPD1 Expression by CD4+Foxp3+ Regulatory T Cells Promotes Hepatic Metastatic Tumor Growth in Mice", Gastroenterology (2010) 139(3):1030-1040.
Syed et al., "Ectonucleotidase NTPDase3 is abundant in pancreatic beta-cells and regulates glucose-induced insulin secretion", Endocrin. Metabol. (2013) 305(10): E1319-1326.
Taylor et al., "Human immunoglobulin transgenes undergo rearrangement, somatic mutation and class switching in mice that lack endogenous IgM". Int Immunol. (1994) 6(4):579-591.
Thotakura et al., "Enzymatic Deglycosylation of glycoproteins", Meth Enzymol. (1987) 138:350-359.
Traverso et al., "Analysis of Regulatory T Cells in Patients Affected by Renal Cell Carcinoma", The Journal of Urology (2010) 183(4): Suppl. Abstract 365 in 2 pages.
Van Amelsfort et al., "CD4+CD25+ Regulatory T Cells in Rheumatoid Arthritis", Arth Rheum. (2004) 50(9): 2775-2785.
Verhoeyen et al., "Reshaping Human Antibodies: Grafting an Antilysozyme Activity", Science (1988) 239: 1534-1536.
Von Heijne G., "Sequence Analysis in Molecular Biology—Treasure Trove or Trivial Pursuit", Academic Press, Inc. (1987) TOC.
Urlaub et al., Isolation of Chinese hamster cell mutants deficient in dihydrofolate reductase activity, Proc Natl Acad Sci. USA (1980) 77(7):4216-4220.

Wang et al., "Identification of a Fab interaction footprint site on an icosahedral virus by cryoelectron microscopy and X-ray crystallography", Nature (1992) 355: 275-278.
Wang et al., "CD39 Is an Exto-(Ca2+,Mg2+)-apyrase", J Biol Chem. (1996) 271(17):9898-9901.
Ward et al., "Binding activities of a repertoire of single immunoglobulin variable domains secreted from *Escherichia coli*", Nature (1989) 341: 544-546.
Wells J.A., "Binding in the growth hormone receptor complex", PNAS USA (1996) 93: 1-6.
Whiteside et al., "The role of the adenosinergic pathway in immunosuppression mediated by human regulatory T cells (Treg)", Curr Med Chem. (2011) 18(34):5217-5223.
Whiteside et al., "Disarming suppressor cells to improve immunotherapy", Cancer Immunol Immunother. (2012) 61(2):283-288.
Wu et al., "Multimerization of a chimeric anti-CD20 single-chain Fv-Fc fusion protein is mediated through variable domain exchange", Prot Engin. (2001) 14(12):1015-1033.
Wu, "RanBPM associates with CD39 and modulates ecto-nucleotidase activity," Biochem. J. (2006) 396(1): 23-30.
Yamaguchi et al., "Manipulation of Tumour Immunity Targeting CD25+ CD4+ regulatory T-cells", Experimental Med. (2007) 25(18): 2868-2874.
Young et al., "Co-inhibition of CD73 and A2AR Adenosine Signaling Improves Anti-tumor Immune Responses", Cancer Cell (Sep. 2016) 30(3):391-403.
Yeung et al., "CD39L2, A Gene encoding a human nucleoside diphosphatase, predominantly expressed in the heart", Biochem. (2000) 39: 12916-12923.
Zhang et al., "CD73: Anovel Target for Cancer Immunotherapy", Cancer Res. (2010), 70(16):6407-6411.
International Search Report and Written Opinion dated Jun. 4, 2009 in PCT/EP2009/051078.
International Search Report and Written Opinion dated Feb. 24, 2012 in PCT/EP2011/073659.
U.S. Office Action dated Jul. 20, 2012 in U.S. Appl. No. 12/863,461, filed Jul. 19, 2010.
U.S. Response dated Aug. 14, 2012 in U.S. Appl. No. 12/863,461, filed Jul. 19, 2010.
U.S. Office Action dated Oct. 1, 2012 in U.S. Appl. No. 12/863,461, filed Jul. 19, 2010.
U.S. Response dated Jan. 31, 2013 in U.S. Appl. No. 12/863,461, filed Jul. 19, 2010.
U.S. Office Action dated Mar. 6, 2013 in U.S. Appl. No. 12/863,461, filed Jul. 19, 2010.
U.S. Response dated Jun. 19, 2013 in U.S. Appl. No. 12/863,461, filed Jul. 19, 2010.
U.S. Notice of Allowance dated Aug. 19, 2013 in U.S. Appl. No. 12/863,461, filed Jul. 19, 2010.
U.S. Response dated Nov. 14, 2013 in U.S. Appl. No. 12/863,461, filed Jul. 19, 2010.
U.S. Office Action dated Nov. 21, 2013 in U.S. Appl. No. 12/863,461, filed Jul. 19, 2010.
U.S. Response dated Feb. 19, 2014 in U.S. Appl. No. 12/863,461, filed Jul. 19, 2010.
U.S. Office Action dated Mar. 18, 2014 in U.S. Appl. No. 12/863,461, filed Jul. 19, 2010.
U.S. Response dated Jun. 18, 2014 in U.S. Appl. No. 12/863,461, filed Jul. 19, 2010.
U.S. Office Action dated Jul. 10, 2014 in U.S. Appl. No. 12/863,461, filed Jul. 19, 2010.
U.S. Response dated Sep. 18, 2014 in U.S. Appl. No. 12/863,461, filed Jul. 19, 2010.
U.S. Office Action dated Oct. 2, 2014 in U.S. Appl. No. 12/863,461, filed Jul. 19, 2010.
U.S. Response dated Feb. 20, 2015 in U.S. Appl. No. 12/863,461, filed Jul. 19, 2010.
U.S. Office Action dated Mar. 18, 2015 in U.S. Appl. No. 12/863,461, filed Jul. 19, 2010.
U.S. Response dated Aug. 18, 2015 in U.S. Appl. No. 12/863,461, filed Jul. 19, 2010.

(56) References Cited

OTHER PUBLICATIONS

U.S. Office Action dated Oct. 5, 2015 in U.S. Appl. No. 12/863,461, filed Jul. 19, 2010.
U.S. Response dated Jan. 21, 2016 in U.S. Appl. No. 12/863,461, filed Jul. 19, 2010.
U.S. Office Action dated Mar. 22, 2016 in U.S. Appl. No. 12/863,461, filed Jul. 19, 2010.
U.S. Response dated Jul. 21, 2016 in U.S. Appl. No. 12/863,461, filed Jul. 19, 2010.
U.S. Office Action dated Oct. 26, 2016 in U.S. Appl. No. 12/863,461, filed Jul. 19, 2010.
U.S. Response/AFCP dated Nov. 30, 2016 in U.S. Appl. No. 12/863,461, filed Jul. 19, 2010.
U.S. Advisory Action dated Dec. 27, 2016 in U.S. Appl. No. 12/863,461, filed Jul. 19, 2010.
U.S. Final Response/RCE dated Jan. 26, 2017 in U.S. Appl. No. 12/863,461, filed Jul. 19, 2010.
U.S. Office Action dated May 4, 2017 in U.S. Appl. No. 12/863,461, filed Jul. 19, 2010.
U.S. Response dated Oct. 3, 2017 in U.S. Appl. No. 12/863,461, filed Jul. 19, 2010.
U.S. Office Action dated Dec. 1, 2017 in U.S. Appl. No. 12/863,461, filed Jul. 19, 2010.
U.S. Response dated May 31, 2018 in U.S. Appl. No. 12/863,461, filed Jul. 19, 2010.
U.S. Office Action dated Jul. 30, 2018 in U.S. Appl. No. 12/863,461, filed Jul. 19, 2010.
U.S. Preliminary Amendment dated Jun. 20, 2013 in U.S. Appl. No. 13/996,097, filed Jun. 20, 2013.
U.S. Restriction Requirement dated May 8, 2014 in U.S. Appl. No. 13/996,097, filed Jun. 20, 2013.
U.S. Response to Restriction dated Jul. 8, 2014 in U.S. Appl. No. 13/996,097, filed Jun. 20, 2013.
U.S. Office Action dated Sep. 29, 2014 in U.S. Appl. No. 13/996,097, filed Jun. 20, 2013.
U.S. Response dated Mar. 2, 2015 in U.S. Appl. No. 13/996,097, filed Jun. 20, 2013.
U.S. Office Action dated May 1, 2015 in U.S. Appl. No. 13/996,097, filed Jun. 20, 2013.
U.S. Response dated Oct. 8, 2015 in U.S. Appl. No. 13/996,097, filed Jun. 20, 2013.
U.S. Office Action dated Aug. 16, 2016 in U.S. Appl. No. 13/996,097, filed Jun. 20, 2013.
U.S. Response dated Nov. 18, 2016 in U.S. Appl. No. 13/996,097, filed Jun. 20, 2013.
U.S. Office Action dated Dec. 20, 2016 in U.S. Appl. No. 13/996,097, filed Jun. 20, 2013.
U.S. Response dated Apr. 20, 2017 in U.S. Appl. No. 13/996,097, filed Jun. 20, 2013.
U.S. Office Action dated Jun. 8, 2017 in U.S. Appl. No. 13/996,097, filed Jun. 20, 2013.
U.S. Response dated Sep. 7, 2017 in U.S. Appl. No. 13/996,097, filed Jun. 20, 2013.
U.S. Office Action dated Dec. 13, 2017 in U.S. Appl. No. 13/996,097, filed Jun. 20, 2013.
U.S. Response dated Jun. 8, 2018 in U.S. Appl. No. 13/996,097, filed Jun. 20, 2013.
U.S. Office Action dated Sep. 17, 2018 in U.S. Appl. No. 13/996,097, filed Jun. 20, 2013.
Notice of Appeal filed Mar. 15, 2019 in U.S. Appl. No. 13/996,097, filed Jun. 20, 2013.
Appeal Brief filed Jun. 10, 2019 and Revision filed Jul. 8, 2019 in U.S. Appl. No. 13/996,097, filed Jun. 20, 2013.
European Notice of Opposition by AbbVie, Inc. dated Feb. 15, 2019 against EP Patent No. 2654789, granted May 30, 2018 (4 pages).
European Opposition Brief by AbbVie, Inc. dated Feb. 26, 2019 against EP Patent No. 2654789, granted May 30, 2018 (35 pages).
European Notice of Opposition by Tizona Therapeutics, Inc. dated Feb. 15, 2019 against EP Patent No. 2654789, granted May 30, 2018 (6 pages).
European Opposition Brief by Tizona Therapeutics, Inc. dated Feb. 26, 2019 against EP Patent No. 2654789, granted May 30, 2018 (25 pages).
European Notice of Opposition by D Young & Co LLP. dated Feb. 28, 2019 against EP Patent No. 2654789, granted May 30, 2018 (8 pages).
European Opposition Brief by D Young & Co LLP dated Feb. 28, 2019 against EP Patent No. 2654789, granted May 30, 2018 (53 pages).
European Notice of Opposition by Boult Wade Tennant LLP. dated Feb. 28, 2019 against EP Patent No. 2654789, granted May 30, 2018 (8 pages).
European Opposition Brief by Boult Wade Tennant LLP dated Feb. 28, 2019 against EP Patent No. 2654789, granted May 30, 2018 (25 pages).
Alaibac M., "Ultra-low dosage regimen of Rituximab in autoimmune blistering skin conditions". Front Immunol. Apr. 18, 2018;9:Article 810.
Beyer et al., "Crystal structures of the pro-inflammatory cytokine interleukin-23 and its complex with a high-affinity neutralizing antibody." J Mol Biol. (2008) 382(4): 942-955.
Bowers et al., "Crystal structures of the pro-inflammatory cytokine interleukin-23 and its complex with a high-affinity neutralizing antibody." J Biol Chem. (2014) 289: 33557-33567.
Casset et al., "A peptide mimetic of an anti-CD4 monoclonal antibody by rational design", Biochem Biophys Res Commun. (2003) 307(1): 198-205.
CDC—Centers for Disease Control & Prevention, "What is Colorectal Cancer?", downloaded from https://www.cdc.gov/cancer/colorectal/basic_info/what-is-colorectal-cancer.htm#: on Feb. 17, 2022, 1 page.
Dees et al., "Regulatory T cell targeting in cancer: Emerging strategies in immunotherapy". Eur J Immunol. Feb. 2021;51(2):280-291.
Ghiringhelli et al., "CD4+CD25+ regulatory T cells suppress tumor immunity but are sensitive to cyclophosphamide which allows immunotherapy of established tumors to be curative". Eur J Immunol. Feb. 2004;34(2):336-344.
Hato et al., "Molecular Pathways: The Immunogenic Effects of Platinum-Based Chemotherapeutics", Clin Cancer Res. (2014) 20(11): 2831-2837.
Jardine et al., "Rational HIV immunogen design to target specific germline B cell receptors." Science (2013) 340: 711-716.
Jørgensen J.T., "PD-L1 expression and efficacy of pembrolizumab as monotherapy in NSCLC". Chin Clin Oncol. Feb. 11, 2020;9(4):60 (5 pages).
Kim et al., "PD-L1 expression on immune cells, but not on tumor cells, is a favorable prognostic factor for head and neck cancer patients". Sci Reports. Nov. 14, 2016;6(1):12 pages.
Larsen et al., "Crystal structure of a cocaine-binding antibody." J Mol Biol. (2001) 311(1): 9-15.
Lévesque et al., "Specificity of the ecto-ATPase inhibitor ARL 67156 on human and mouse ectonucleotidases." Br. J. Pharmacol. (2007) 152: 141-150.
Marchenko et al., "Prognostic value of regulatory T cells and T helper 17 cells in high grade serous ovarian carcinoma". J Cancer Res Clin Oncol. Jun. 28, 2022:1-4.
Merck & Co., "KEYRUDA. Summary of Product Characteristics", 2022; 130 pages.
Merck & Co., "KEYRUDA: PD-L1 Expression Testing Information"; 2022; 19 pages.
Möller et al., "Tumor cell PD-L1 expression is a strong predictor of unfaborable prognosis in immune checkpoint therapy-naive clear cell renal cell cancer". Int'l Urol Neph. Dec. 2021;53(12):2493-2503.
Nicoletto et al., "Phase II Study of Pegylated Liposomal Doxorubicin and Oxaliplatin in Relapsed Advanced Ovarian Cancer", Gynecol Oncol. (2006) 100(2): 318-323.
Rudikoff et al., "Single amino acid substitution altering antigen-binding specificity", PNAS (1982) 79(6): 1979-1983.
Shi et al., "Interactive effects of PD-LI expression in tumor and immune cells on prognosis of esophageal squamous cell carcinoma: A one-center retrospective cohort study". OncoTargets Ther. 2020;13:6565 (8 pages).

(56) References Cited

OTHER PUBLICATIONS

Taylor et al., "Oxaliplatin salvage for recurrent ovarian cancer: A single institution's experience in patient populations with platinum resistant disease or a history of platinum hypersensitivity", Gyn Oncol. (Jul. 1, 2014) 134(1): 68-72.
Teplyakov et al., "Antibody modeling assessment II. Structures and models." Proteins: Struct, Function Bioinfo. (2014) 82(8): 1563-1582.
Ultsch et al., "Structural basis of signaling blockade by anti-IL-13 antibody lebrikizumab." J Mol Biol. (2013) 425(8): 1330-1339.
Yegutkin et al., "Metabolism of circulating ADP in the bloodstream is mediated via integrated actions of soluble adenylate kinase-1 and NTPDase1/CD39 activities." FASEB J. (2012) 26(9): 3875-3883.
Examiner's Answer on Appeal Brief dated Nov. 7, 2019 in U.S. Appl. No. 13/996,097, filed Jun. 20, 2013.
PTAB Decision on Appeal dated Oct. 29, 2020 in U.S. Appl. No. 13/996,097, filed Jun. 20, 2013.
U.S. Office Action dated May 11, 2020 in U.S. Appl. No. 15/778,202, filed May 22, 2018.
U.S. Response dated Jan. 25, 2021 in U.S. Appl. No. 15/778,202, filed May 22, 2018.
U.S. Office Action dated Feb. 5, 2021 in U.S. Appl. No. 15/778,202, filed May 22, 2018.
U.S. Response dated Jul. 6, 2021 in U.S. Appl. No. 15/778,202, filed May 22, 2018.
U.S. Office Action dated Jul. 15, 2021 in U.S. Appl. No. 15/778,202, filed May 22, 2018.
U.S. Response dated Nov. 29, 2021 in U.S. Appl. No. 15/778,202, filed May 22, 2018.
U.S. Office Action dated Dec. 14, 2021 in U.S. Appl. No. 15/778,202, filed May 22, 2018.
U.S. Response dated Mar. 25, 2022 in U.S. Appl. No. 15/778,202, filed May 22, 2018.
U.S. Notice of Allowance dated Apr. 13, 2022 in U.S. Appl. No. 15/778,202, filed May 22, 2018.
U.S. Notice of Abandonment dated Aug. 24, 2022 in U.S. Appl. No. 15/778,202, filed May 22, 2018.
U.S. Office Action dated Apr. 7, 2021 in U.S. Appl. No. 16/370,726, filed Mar. 29, 2019.
U.S. Response dated Aug. 9, 2021 in U.S. Appl. No. 16/370,726, filed Mar. 29, 2019.
U.S. Office Action dated Oct. 12, 2021 in U.S. Appl. No. 16/370,726, filed Mar. 29, 2019.
U.S. Response dated Feb. 11, 2022 in U.S. Appl. No. 16/370,726, filed Mar. 29, 2019.
U.S. Notice of Allowance dated May 25, 2022 in U.S. Appl. No. 16/370,726, filed Mar. 29, 2019.
U.S. Response (Express Abandonment) dated Jul. 28, 2022 in U.S. Appl. No. 16/370,726, filed Mar. 29, 2019.
U.S. Office Action dated Nov. 30, 2020 in U.S. Appl. No. 16/370,789, filed Mar. 29, 2019.
U.S. Response dated May 27, 2021 in U.S. Appl. No. 16/370,789, filed Mar. 29, 2019.
U.S. Office Action dated Jul. 27, 2021 in U.S. Appl. No. 16/370,789, filed Mar. 29, 2019.
U.S. Response dated Jan. 27, 2022 in U.S. Appl. No. 16/370,789, filed Mar. 29, 2019.
U.S. Office Action dated May 19, 2022 in U.S. Appl. No. 16/370,789, filed Mar. 29, 2019.
U.S. Response dated Nov. 11, 2022 in U.S. Appl. No. 16/370,789, filed Mar. 29, 2019.
U.S. Office Action dated Apr. 19, 2021 in U.S. Appl. No. 16/443,744, filed Jun. 17, 2019.
U.S. Response dated Jul. 20, 2021 in U.S. Appl. No. 16/443,744, filed Jun. 17, 2019.
U.S. Office Action dated Aug. 3, 2021 in U.S. Appl. No. 16/443,744, filed Jun. 17, 2019.
U.S. Response dated Jan. 27, 2022 in U.S. Appl. No. 16/443,744, filed Jun. 17, 2019.
U.S. Notice of Allowance dated Feb. 18, 2022 in U.S. Appl. No. 16/443,744, filed Jun. 17, 2019.
U.S. Office Action dated Sep. 21, 2021 in U.S. Appl. No. 16/477,506, filed Jul. 11, 2019.
U.S. Response filed Jan. 20, 2022 in U.S. Appl. No. 16/477,506, filed Jul. 11, 2019.
U.S. Office Action dated Mar. 21, 2022 in U.S. Appl. No. 16/477,506, filed Jul. 11, 2019.
U.S. Response dated Aug. 19, 2022 in U.S. Appl. No. 16/477,506, filed Jul. 11, 2019.
U.S. Supplemental Response dated Sep. 12, 2022 in U.S. Appl. No. 16/477,506, filed Jul. 11, 2019.
U.S. Notice of Allowance dated Oct. 13, 2022 in U.S. Appl. No. 16/477,506, filed Jul. 11, 2019.
Patent Proprietor's Response dated Sep. 19, 2019 to AbbVie, Inc. Opposition in re EP 2654789, granted May 30, 2018 (30 pages).
Opposer's Reply to Patent Proprietor's Response dated Oct. 17, 2019 in re EP 2654789, granted May 30, 2018 (36 pages).
European Decision Revoking EP Patent No. 2654789 issued by EPO on Apr. 1, 2022 following Opposition by Opposers (122 pages).
Patent Proprietor's Notice and Grounds of Appeal against EPO decision dated Aug. 10, 2022 in Oppositions filed against EP Patent No. 2654789, granted May 30, 2018 (13 pages).
Opposer AbbVie Inc.'s Reply to Patent Proprietor's Appeal [T1388/22] of Opposition Decision dated Dec. 20, 2022 in re EP 2654789, granted May 30, 2018 (48 pages).
Opposer Boult Wade Tennant LLP's Reply to Patent Proprietor's Appeal [T1388/22] of Opposition Decision dated Dec. 20, 2022 in re EP 2654789, granted May 30, 2018 (35 pages).
Opposer D. Young & Co.'s Reply to Patent Proprietor's Appeal [T1388/22] of Opposition Decision dated Dec. 21, 2022 in re EP 2654789, granted May 30, 2018 (36 pages).
Opposer Tizona Therapeutics, Inc.'s Reply to Patent Proprietor's Appeal [T1388/22] of Opposition Decision dated Dec. 21, 2022 in re EP 2654789, granted May 30, 2018 (47 pages).

\* cited by examiner

ANTIBODIES AGAINST HUMAN CD39 AND USE THEREOF FOR INHIBITING T REGULATORY CELLS ACTIVITY

The present application is a continuation application of U.S. patent application Ser. No. 14/939,650, filed Nov. 12, 2015, now U.S. Pat. No. 10,662,253, which is a division application of U.S. patent application Ser. No. 12/863,461, filed Jul. 19, 2010, which was filed pursuant to 35 U.S.C. 371 as a U.S. National Phase application of International Patent Application No. PCT/EP09/51078, filed Jan. 30, 2009, claiming the benefit of priority to European Patent Application No. 08300061.2, filed on Jan. 31, 2008, and European Patent Application No. 08162683.0, filed on Aug. 20, 2008. The entire text of the aforementioned applications is incorporated herein by reference in its entirety.

FIELD OF THE INVENTION

The invention relates to antibodies against human CD39 for inhibiting T regulatory cells (Treg) activity.

A Substitute Sequence Listing submitted as an ASCII text filed via EFS-Web is hereby incorporated by reference in accordance with 35 U.S.C. § 1.52(e). The name of the ASCII text file for the Substitute Sequence Listing is INNAT_020C1 Sequence_Listing.TXT, the date of creation of the ASCII text file is Sep. 23, 2020 and the size of the ASCII text file is 14.0 kb.

BACKGROUND OF THE INVENTION

T regulatory cells (Treg cells) are currently classified into two main subsets, according to their origin and suppressive activity (Bluestone, J. A. & Abbas, A. K. Natural versus adaptive regulatory T cells. Nature Rev. Immunol. 3, 253-257 (2003)). Natural Treg cells originate in the thymus by high-affinity interaction of the T-cell receptor (TCR) with antigens expressed in the thymic stroma. They have been classically described to suppress the proliferation of effector T cells in vitro in a contact-dependent, cytokine-independent manner. Natural Treg cells constitutively express CD25, cytotoxic T-lymphocyte antigen 4 (CTLA4), glucocorticoid-induced tumour necrosis factor (TNF) receptor (GITR) and OX40, molecules that characterize activated lymphocytes. However, the high-level expression of the transcription factor FOXP3 (forkhead box p3) is the most distinctive marker for the regulatory lineage, at least in the murine system. Although incompletely characterized to date, the network of natural Treg-cell suppression mechanisms includes surface molecules such as CTLA4, membrane-bound transforming growth factor (TGF) and the pericellular generation of adenosine.

Depletion of naturally occurring Treg cells in normal hosts results in various autoimmune diseases because the host immune system is unchecked and goes to attack the body's own tissue. In rodents, reduction or functional alteration of CD25+CD4+ regulatory T cells has been shown to cause the spontaneous development of various organ-specific autoimmune diseases including thyroiditis, gastritis, and type 1 diabetes. Regulatory T cells are also critical for the controlled response to environmental antigens and have been shown to prevent inflammatory bowel disease (IBD) as well as allergy.

Treg have now been described in a large number of systems and have emerged as a major mechanism for the maintenance of self-tolerance and protection from autoimmune disease. Whereas Treg limit autoimmunity, they also attenuate the potency of anti-tumor and anti-viral immunity. For example, in the case of cancer, Treg cells may have a negative influence since they could hamper normally desirable antitumour immune responses and there is indeed already some evidence to suggest that cancer patients show increased numbers of active Treg cells specific for tumour proteins both in their blood and within the tumours themselves. Indeed several recent studies in human, reported elevated percentages of CD4+CD25+ Treg cells in a variety of cancers including lung cancer, breast cancer, ovarian cancer, melanoma, liver cancer, gastric cancer and lymphoma. In the case of viral infections, higher numbers of Treg cells have been reported in individuals who are chronically infected with hepatitis C and hepatitis B virus and in patients infected with human immunodeficiency virus.

Accordingly, methods and compositions for the inhibition or elimination of Treg activity would be useful in the treatment of diseases and disorders characterized by an increased Treg activity, e.g., cancer, infectious disease and immune response.

A recent study demonstrates that CD39 might represent a target for the development of novel therapeutic methods useful for treating diseases associated with Treg activity (Deaglio S, Dwyer K M, Gao W, Friedman D, Usheva A, Erat A, Chen J F, Enjyoji K, Linden J, Oukka M, Kuchroo V K, Strom T B, Robson S C. Adenosine generation catalyzed by CD39 and CD73 expressed on regulatory T cells mediates immune suppression. J Exp Med. 2007 Jun. 11; 204(6):1257-65. Epub 2007 May 14). The authors indeed showed that CD39 is a cell surface marker of Foxp3 Treg cells which may regulate immune T cell suppression by the downstream production of adenosine.

SUMMARY OF THE INVENTION

The present invention relates to a CD39 antibody for the treatment or prevention of diseases associated with an increased T regulatory cell (Treg) activity.

In particular, the invention relates to a CD39 antibody for the treatment or prevention of cancers and infectious diseases.

The invention also relates to a pharmaceutical composition for the treatment or prevention of diseases associated with an increased T regulatory cell (Treg) activity comprising a CD39 antibody.

DETAILED DESCRIPTION OF THE INVENTION

Definitions

The term "CD39" denotes the CD39 protein also named as ectonucleoside triphosphate diphosphohydrolase-1 (EN-TPD1). CD39 is an ectoenzyme that hydrolases ATP/UTP and ADP/UDP to the respective nucleosides such as AMP.

The term "CD39 antibody" refers to an antibody directed against human CD39.

According to the present invention, "antibody" or "immunoglobulin" have the same meaning, and will be used equally in the present invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fe receptors (FeR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

According to the invention, the term "chimeric antibody" refers to an antibody which comprises a VH domain and a VI domain of a CD39 antibody from any species, preferably mouse, and a CH domain and a CL domain of a human antibody.

According to the invention, the term "humanized antibody" refers to an antibody having variable region framework and constant regions from a human antibody but retains the CDRs of a CD39 antibody from any species, preferably mouse.

The term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 and antigen binding activity, which is slightly larger than the Fab bound via a disulfide bond of the hinge region, among fragments obtained by treating IG with a protease, pepsin.

The term "Fab'" refers to an antibody fragment having a molecular weight of about 50,000 and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to a polypeptide (i.e. an antibody according to the invention) or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

The term "disease associated with an increased Teg activity" encompasses all disorders that are associated with, caused by, or result from an increased Treg activity.

In the context of the invention, the term "treating" or "treatment", as used herein, means reversing, alleviating, inhibiting the progress of, or preventing the disorder or condition to which such term applies, or one or more symptoms of such disorder or condition. A "therapeutically effective amount" is intended for a minimal amount of active agent (e.g., CD39 antibodies) which is necessary to impart therapeutic benefit to a subject. For example, a "therapeutically effective amount" to a mammal is such an amount which induces, ameliorates or otherwise causes an improvement in the pathological symptoms, disease progression or physiological conditions associated with or resistance to succumbing to a disorder.

As used herein, the term "prevention" refers to preventing the disease or condition from occurring in a subject which has not yet been diagnosed as having it.

As used herein, the term "subject" denotes a mammal, such as a rodent, a feline, a canine, and a primate. Preferably a subject according to the invention is a human.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

Therapeutic Uses of CD39 Antibodies

The inventors have demonstrated that antibodies directed against CD39, including the CD39 antibody called BY40, are able to inhibit the Treg activity. Thus, they propose to use CD39 antibodies for inhibiting Treg activity, for the treatment or prevention of diseases associated with an increased Treg activity.

Therefore, a first aspect of the invention provides methods and pharmaceutical compositions for the treatment or prevention of diseases associated with an increased Treg activity.

The invention thus relates to a CD39 antibody for the treatment or prevention of diseases associated with an increased Treg activity.

The invention also relates to a method for treating or preventing a disease associated with an increased Treg activity which comprises the step of administering to a subject in need thereof a CD39 antibody.

Examples of diseases associated with an increased Treg activity includes but are not limited to cancer and infectious diseases. Examples of cancers include but are not limited to lung cancer, breast cancer, ovarian cancer, melanoma, liver cancer, gastric cancer and lymphoma. Infectious diseases include but are not limited to infection with virus such as human immunodeficiency virus, Hepatitis B virus, hepatitis C virus, with parasites such as *Plasmodium Falciparum* (causative agent for Malaria), or with bacteria such as *Mycobacterium tuberculosis*.

CD39 antibodies may be also used to inhibit or to deplete regulatory T cells during ex vivo expansion of tumor specific cytotoxic lymphocytes before re-administration to patients who developed cancer: inhibition of Treg as a strategy for the ex vivo generation of antigen-specific T cells for adoptive cellular therapy.

CD39 antibodies may be also used as an adjuvant of vaccine compositions. Vaccine compositions are indeed suitable for the treatment of cancer or infectious disease. However, their therapeutic efficiency may be limited due to the induction of Treg. Therefore administration of CD39 antibodies in combination with administration of vaccine composition may be useful to enhance the efficiency of said vaccines compositions.

The present invention contemplates the use of any CD39 antibody or fragment thereof, including CD39 chimeric antibodies (preferably chimeric mouse/human antibodies) or humanized CD39 antibodies, provided that said antibody inhibits the Treg activity.

In a particular embodiment, said CD39 antibody may be obtainable from the hybridoma deposited as CNCM-I-3889.

In another embodiment, said CD39 antibody may comprises the VL chain of the antibody obtainable from hybridoma deposited as CNCM-I-3889 and the VH chain of the antibody obtainable from hybridoma deposited as CNCM-I-3889.

In another embodiment, said CD39 antibody may comprise a variable light chain (VL) comprising the CDRs of the VL chain of the antibody obtainable from hybridoma deposited as CNCM-I-3889 and a variable heavy chain (VH) comprising the CDRs of the VH chain of the antibody obtainable from hybridoma deposited as CNCM-I-3889.

In another embodiment of the invention, said CD39 antibody may comprise a first heavy chain CDR sequence as set forth in SEQ ID NO:2, a second heavy chain CDR sequence as set forth in SEQ ID NO:3, and a third heavy chain CDR sequence as set forth in SEQ ID NO:4; and a first light chain CDR sequence as set forth in SEQ ID NO:6, a second light chain CDR sequence as set forth in SEQ ID NO:7, and a third light chain CDR sequence as set forth in SEQ ID NO:8. In a particular embodiment, the heavy chain variable domain of said antibody has the amino acid sequence as set forth in SEQ ID NO: 1 and/or the light chain variable domain of said antibody has the amino acid sequence set forth in SEQ ID NO: 5.

In a particular embodiment, said CD39 antibody is a chimeric antibody, preferably a chimeric mouse/human antibody.

In particular, said mouse/human chimeric antibody may comprise the variable domains of an antibody obtainable from hybridoma deposited as CNCM-I-3889.

In another embodiment, said CD39 antibody is a humanized antibody.

In particular, in said humanized antibody, the variable domain comprises human acceptor frameworks regions, and optionally human constant domain where present, and non-human donor CDRs, such as mouse CDRs of an antibody obtainable from hybridoma deposited as CNCM-1-3889.

The invention contemplates use of fragments of said CD39 antibodies which include but are not limited to Fv, Fab, F(ab')2, Fab', dsFv, scFv, sc(Fv)2 and diabodies; and multispecific antibodies formed from antibody fragments.

CD39 antibodies may be produced by any technique known in the art, such as, without limitation, any chemical, biological, genetic or enzymatic technique, either alone or in combination.

For example, CD39 antibodies can be raised according to known methods by administering the appropriate antigen or epitope to a host animal selected, e.g., from pigs, cows, horses, rabbits, goats, sheep, and mice, among others.

Various adjuvants known in the art can be used to enhance antibody production. Although antibodies useful in practicing the invention can be polyclonal, monoclonal antibodies are preferred. Monoclonal antibodies against CD39 can be prepared and isolated using any technique that provides for the production of antibody molecules by continuous cell lines in culture.

Techniques for production and isolation include but are not limited to the hybridoma technique originally described by Kohler and Milstein (1975); the human B-cell hybridoma technique (Cote et al., 1983); and the EBV-hybridoma technique (Cole et al. 1985).

Knowing the amino acid sequence of the desired antibody, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, CD39 antibodies can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

In particular, the invention further relates to a method of producing an antibody of the invention, which method comprises the steps consisting of: (i) culturing a cell expressing a CD39 antibody under conditions suitable to allow expression of said antibody; and (ii) recovering the expressed antibody.

In another particular embodiment, the method comprises the steps of:

(i) culturing an hybridoma expressing a CD39 antibody, (e.g. the hybridoma deposited as CNCM-1-3889), under conditions suitable to allow expression of antibody; and (ii) recovering the expressed antibody.

CD39 antibodies are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, a human chimeric CD39 antibody invention can be produced by obtaining nucleic sequences encoding VL and VI domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See Morrison S L. et al. (1984) and patent documents U.S. Pat. Nos. 5,202,238; and 5,204,244).

A CD39 humanized antibody may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred (Shitara K et al. 1994). Examples of tandem type humanized antibody expression vector include pKANTEX93 (WO 97/10354), pEE18 and the like.

Methods for producing humanized antibodies based on conventional recombinant DNA and gene transfection techniques are well known in the art (See, e. g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519,596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

Fab can be obtained by treating an antibody which specifically reacts with human CD39 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

F(ab')2 can be obtained treating an antibody which specifically reacts with human CD39 with a protease, pepsin. Also, the F(ab')2 can be produced by binding Fab' described below via a thioether bond or a disulfide bond.

Fab' can be obtained treating F(ab')2 which specifically reacts with human CD39 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

scFv can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e. g., WO98/45322; WO 87/02671; U.S. Pat. Nos. 5,859,205; 5,585,089; 4,816,567; EP0173494).

Amino acid sequence modification(s) of the antibodies described herein are contemplated. For example, it may be desirable to improve the binding affinity and/or other biological properties of the antibody. It is known that when a humanized antibody is produced by simply grafting only CDRs in VH and VL of an antibody derived from a non-human animal in FRs of the VH and VL of a human antibody, the antigen binding activity is reduced in comparison with that of the original antibody derived from a non-human animal. It is considered that several amino acid residues of the VH and VL of the non-human antibody, not only in CDRs but also in FRs, are directly or indirectly associated with the antigen binding activity. Hence, substitution of these amino acid residues with different amino acid residues derived from FRs of the VH and VL of the human antibody would reduce of the binding activity. In order to resolve the problem, in antibodies grafted with human CDR, attempts have to be made to identify, among amino acid sequences of the FR of the VH and VL of human antibodies, an amino acid residue which is directly associated with binding to the antibody, or which interacts with an amino acid residue of CDR, or which maintains the three-dimensional structure of the antibody and which is directly associated with binding to the antigen. The reduced antigen binding activity could be increased by replacing the identified amino acids with amino acid residues of the original antibody derived from a non-human animal.

Modifications and changes may be made in the structure of the antibodies of the present invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (−2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further object of the present invention also encompasses function-conservative variants of the antibodies of the present invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably grater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. Another type of amino acid modification of the antibody of the invention may be useful for altering the original glycosylation pattern of the antibody.

By "altering" is meant deleting one or more carbohydrate moieties found in the antibody, and/or adding one or more glycosylation sites that are not present in the antibody.

Glycosylation of antibodies is typically N-linked. "N-linked" refers to the attachment of the carbohydrate moiety to the side chain of an asparagine residue. The tripeptide sequences asparagine-X-serine and asparagines-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. Addition of glycosylation sites to the antibody is conveniently accomplished by altering the amino acid sequence such that it contains one or more of the above-described tripeptide sequences (for N-linked glycosylation sites).

Another type of covalent modification involves chemically or enzymatically coupling glycosides to the antibody. These procedures are advantageous in that they do not require production of the antibody in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as thoseof cysteine, (d) free hydroxyl groups such as those of serine, threonine, or hydroxyproline, (e) aromatic residues such as those of phenylalanine, tyrosine, or tryptophan, or (f) the amide group of glutamine. For example, such methods are described in WO87/05330.

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Sojahr H. et al. (1987) and by Edge, A S. et al. (1981). Enzymatic cleavage of carbohydrate moieties on antibodies can be achieved by the use of a variety of endo- and exo-glycosidases as described by Thotakura, N R. et al. (1987).

Another type of covalent modification of the antibody comprises linking the antibody to one of a variety of non proteinaceous polymers, eg., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

It may be also desirable to modify the antibody of the invention with respect to effector function, e.g. so as to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing inter-chain disulfide bond formation in this region. The homodimeric antibody thus generated may have improved internalization capability and/or increased complement-mediated cell killing and/or antibody-dependent cellular cytotoxicity (ADCC) (Caron P C. et al. 1992; and Shopes B. 1992)

Pharmaceutical Compositions

The invention also relates to pharmaceutical composition comprising CD39 antibodies for the treatment or prevention of diseases associated with an increased Treg activity.

Therefore, CD39 antibodies may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-3889 solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient. etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

A CD39 antibody can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

CD39 antibodies may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 m) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospholipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on p11, ionic strength and the presence of divalent cations.

The invention also provides kits comprising at least one CD39 antibody, particularly an antibody of the invention. Kits containing CD39 antibodies find use therapeutic assays.

Antibodies and Polypeptides of the Invention

The present invention provides for isolated antibodies or fragments thereof that are directed against human CD39. In particular, the inventors have deposited a murine CD39 antibody (BY40) producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on the 4 Jan. 2008. The deposited hybridoma has CNCM deposit number 1-3889. The inventors have deposited the BA54g antibody producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on the 23 Jun. 2009. The deposited hybridoma has CNCM deposit number CNCM 1-4171. Said CD39 antibody may then be obtainable from the hybridoma deposited under the accession number CNCM 1-4171. The inventors have deposited the BY12 antibody producing hybridoma at the Collection Nationale de Cultures de Microorganismes (CNCM, Institut Pasteur, 25 rue du Docteur Roux, 75724 Paris Cedex 15, France), in accordance with the terms of Budapest Treaty, on the 16th of May, 2018. The deposited hybridoma has CNCM deposit number CNCM 1-5319. Said CD39 antibody may then be obtainable from the hybridoma deposited under the accession number CNCM 1-5319.

A further aspect of the invention thus relates to a murine CD39 antibody (BY40) obtainable from the hybridoma available under CNCM deposit number I-3889.

In another embodiment the antibody of the invention comprises a variable light chain (VL) comprising the CDRs of the VL chain of the antibody obtainable from hybridoma deposited as CNCM-I-3889 and a variable heavy chain (VH) comprising the CDRs of the VH chain of the antibody obtainable from hybridoma deposited as CNCM-I-3889.

In another embodiment the antibody of the invention comprises the VL chain of the antibody obtainable from hybridoma deposited as CNCM-I-3889 and the VH chain of the antibody obtainable from hybridoma deposited as CNCM-I-3889.

The inventors have cloned and characterized the variable domain of the light and heavy chains of said mAb BY40, and thus determined the complementarity determining regions (CDRs) domain of said antibody as described in Table 1:

TABLE 1

VH, VL and CDR domains of mAb BY40, mAb BA54g and mAb BY12

| MAb BY40 Domains | |
|---|---|
| VH | TRVKK PRETV KISCK ASGYT FTHYG MNWVK QAPGK GLKWM GWINT YTGEP TYADD FKGRF AFSLE ASVST AYLQI NNLKN EDTAT YFCAR RRYEG NYVFY YFDYW GQGTT LTVSS AKTTP PSVYP LAPGS AAQTN SMVTL GCLVK GYFPE QVTVT WNSGS LSSGV HTFPA VLQSD LYTLS SSVTV PS (SEQ ID NO: 1) |
| VH CDR 1 | GYTFT HYG (SEQ ID NO: 2) |
| VH CDR2 | INTYT GEP (SEQ ID NO: 3) |
| VH CDR3 | ARRRY EGNYV FYYFD YWGQG TTLTV SS (SEQ ID NO: 4) |
| VL | DIQMT QSPAS LSASV GETVT ITCRA SENIY SYFSW YQQKQ GKSPQ LLVYT AKTLA EGVPS RFSGS GSGTQ FSLKI NSLQP EDFGS YYCQH HYVTP YTFGG GTKLE IKRAD AAPTV SIFPP SSEQL TSGGA SVVCF LNNFY PKDIN VKWKI DGSER QNGVL NSWTD (SEQ ID NO: 5) |

TABLE 1-continued

VH, VL and CDR domains of mAb BY40, mAb BA54g and mAb BY12

| | |
|---|---|
| VL CDR1 | RASEN IYSYF S (SEQ ID NO: 6) |
| VL CDR2 | TAKTL AE (SEQ ID NO: 7) |
| VL CDR3 | QHHYV TPYTF GGGTK LEIKR (SEQ ID NO: 8) |

| MAb BA54g Domains | VH VL and CDR domains of mAb BA54g |
|---|---|
| VH | VH DVQLV ESGGG LVQPG GSRKL SCAAS GFTFS SFGMH WVRQA PEKGL EWVAY ISSGS SIIYY ADTVK GRFTI SRDNP KNTLF LQMTS LGSED TAMYY CARWS TTVVA TDYWG QGTTL TVS (SEQ ID NO: 11) |
| VH CDR1 | GGSRK LSCAA SGFTF SSFGM H (SEQ ID NO: 12) |
| VH CDR2 | YISSG SSIIY YADTV KG (SEQ ID NO: 13) |
| VH CDR3 | WSTTV VATDY WGQGT TLTVS (SEQ ID NO: 14) |
| VL | NIVMT QSPKS MSMSV GERVT LTCKA SENVV TYVSW YQQKP EQSPK LLIYG ASNRY TGVPD RFTGS GSATD FTLTI SSVQA EDLAD YHCGQ GYSYP YTFGG GTKLE IKR (SEQ ID NO: 15) |
| VL CDR1 | KASEN VVTYV S (SEP ID NO: 16) |
| VL CDR2 | GASNR YT (SEQ ID NO: 17) |
| VL CDR3 | CGQGY SYPYT FGGGT KLEIK R (SEQ ID NO: 18) |

| MAb BY12 Domains | VH VL and CDR domains of mAb BY12 |
|---|---|
| VH | QIQLVQSGPELKKPGETVKISCKASGYTFRNYGMNWVKQAPG KGLKWMGWINTYTGEPTYADDFKGRFAFSLATSASTAYLQISN LKNEDTATYFCARKAYYGSNYYFDYWGQGTTLTVSS (SEQ ID NO: 38) |
| VL | DIVMTQSHKFMSTSVGDRVSITCKASQDVSTAVAWYQQKPGQ SPKLLIYSASYRYTGVPDRFTGSGSGTDFTFTISTVQAEDLAVYY CQQHYTTPPYTFGGGTKLEIK (SEQ ID NO: 37) |
| VH CDR1 | NYGMN (SEQ ID NO: 19) |
| VH CDR2 | WINTYTGEPTYADDFKG (SEQ ID NO: 20) |
| VH CDR3 | KAYYGSNYYFDY (SEQ ID NO: 21) |
| VL CDR1 | KASQDVSTAVA (SEQ ID NO: 28) |
| VL CDR2 | SASYRYT (SEQ ID NO: 29) |
| CL CDR2 | QQHYTTPPYT (SEQ ID NO: 30) |

An embodiment of the invention relates to a CD39 antibody comprising a first heavy chain CDR sequence as set forth in SEQ ID NO:2, a second heavy chain CDR sequence as set forth in SEQ ID NO:3, and a third heavy chain CDR sequence as set forth in SEQ ID NO:4; and a first light chain CDR sequence as set forth in SEQ ID NO:6, a second light chain CDR sequence as set forth in SEQ ID NO:7, and a third light chain CDR sequence as set forth in SEQ ID NO:8. In a particular embodiment, the heavy chain variable domain of said antibody has the amino acid sequence as set forth in SEQ ID NO: 1 and/or the light chain variable domain of said antibody has the amino acid sequence set forth in SEQ ID NO: 5.

Antibodies of the invention can be produced by any technique well known in the art. In particular said antibodies are produced by techniques as hereinafter described.

In another embodiment, an antibody of the invention is a chimeric antibody, preferably a chimeric mouse/human antibody. In particular, said mouse/human chimeric antibody may comprise the variable domains of an antibody obtainable from hybridoma deposited as CNCM-I-3889.

An embodiment of the invention relates to the hybridoma accessible under CNCM deposit number 1-3889.

In another embodiment, an antibody of the invention is a humanized antibody. In particular, in said humanized antibody, the variable domain comprises human acceptor frameworks regions, and optionally human constant domain where present, and non-human donor CDRs, such as mouse CDRs as defined above.

The invention further provides fragments of said antibodies which include but are not limited to Fv, Fab, F(ab')2, Fab', dsFv, scFv, sc(Fv)2 and diabodies; and multispecific antibodies formed from antibody fragments.

In another aspect, the invention relates to a polypeptide which has a sequence selected from the group consisting of SEQ ID NO: 1, SEQ ID NO:2, SEQ ID NO:3, SEQ ID NO:4, SEQ ID NO:5; SEQ ID NO: 6; SEQ ID NO:7 and SEQ ID NO:8.

A further object of the invention relates to a nucleic acid sequence encoding an antibody of the invention or a fragment thereof.

In a particular embodiment, the invention relates to a nucleic acid sequence encoding the VH domain of the antibody obtainable from hybridoma deposited as CNCM-I-3889 (BY40) or the VL domain of the antibody obtainable from hybridoma deposited as CNCM-I-3889 (BY40).

In a particular embodiment, the invention relates to a nucleic acid sequence encoding the VH domain of mAb BY40 or the VL domain of mAb BY40.

TABLE 2

Nucleic acids of VH and VL domains of mAb BY40:

| | |
|---|---|
| VH domain: | acg cga gtg aag aag cct cga gag aca gtc aag atc tcc tgc aag gct tct ggg tat acc ttc aca cac tat gga atg aac tgg gtg aag cag gct cca gga aag ggt tta aag tgg atg ggc tgg ata aac acc tac act gga gag cca aca tat gct gac ttc aag gga cgg ttt gcc ttc tct ttg gaa gcc tct gtc agc act gcc tat ttg cag atc aac aac ctc aaa aat gag gac acg gct aca tat ttc tgt gca aga agg aga tat gag ggt aac tac gtt ttt tac tac ttt gac tac tgg ggc caa ggc acc act ctc aca gtc tcc tca (SEQ ID NO: 9) |
| VL domain: | gac atc cag atg act cag tct cca gcc tcc cta tct gca tct gtg gga gaa act gtc acc atc aca tgt cga gca agt gaa aat att tac agt tat ttt tca tgg tat cag cag aaa cag gga aaa tct cct cag ctc ctg gtc tat act gca aaa acc tta gca gaa ggt gtg cca tca agg ttc agt ggc agt gga tca ggc aca cag ttt tct ctg aag atc aac agc ctg cag cct gaa gat ttt ggg agt tat tac tgt caa cat cat tat gtt act ccg tac acg ttc gga ggg ggg acc aag ctg gaa ata aaa cgg (SEQ ID NO: 10) |

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. Nos. 5,882,877, 6,013,516, 4,861,719, 5,278,056 and WO 94/19478.

A further object of the present invention relates to a cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA bas been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli*, *Kluyveromyces* or *Saccharomyces* yeasts, mammalian cell lines (e.g., Vero cells, CIO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag. 20 cell (ATCC CRL1662, hereinafter referred to as "YB2/0 cell"), and the like.

The present invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

Antibodies of the invention can be produced and/or modified by any technique known in the art, as above described.

FIGURES

FIG. 1: Expression of CD39 on $CD4^+CD25^{low}$ and $CD4^+CD25^{high}$ T cells from $HIV^-$ controls and $HIV^+$ patients. Peripheral blood lymphocytes from $HIV^-$ (□▽) controls and $HIV^+$ (■▼) patients were stained with anti-CD39 BY40, anti-CD4 and anti-CD25 mAbs and percentages of $CD39^+$ cells within $CD4^+CD25^{low}$ and $CD4^+CD25^{high}$ populations (A) as well as mean fluorescence intensity (MFI) for CD39 expression in both subpopulations (B) were determined by flow cytometry. Representative overlays comparing the levels of CD39 expression on CD4$^+$CD25$^{low}$(left) and CD4$^+$CD25$^{high}$ (right) T cells from HIV$^+$ (empty histograms) and HIV donors (filled histograms) are represented in C. In A and B, p values assessed by Wilcoxon's and Man-Witney's non-parametric tests are indicated.

Figure 2:
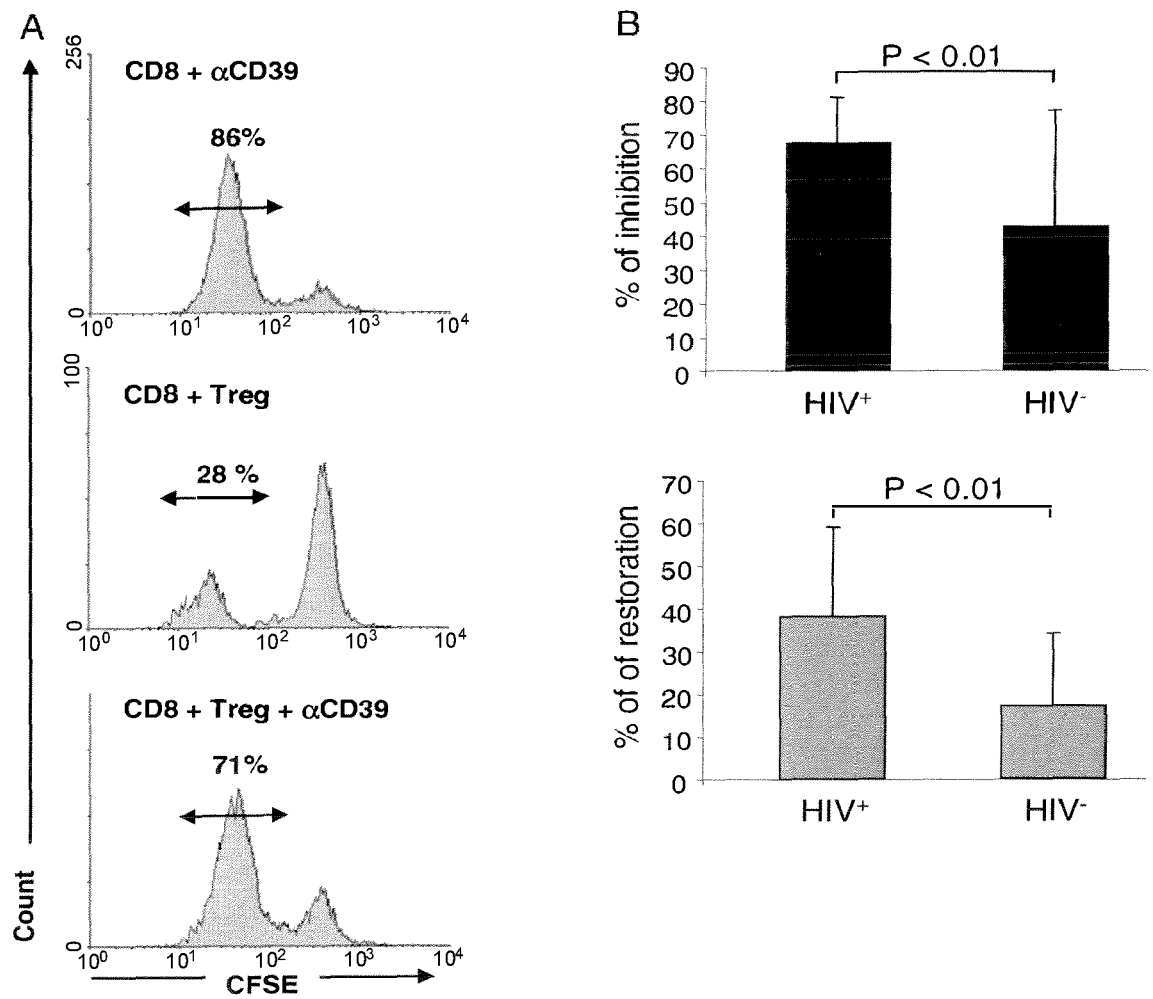

FIG. 2: Effect of the CD39 mAb, BY40, on the immunosuppressive activity of CD4$^+$CD25$^{high}$ regulatory T cells. A. CFSE-labeled CD8 T cells from HIV$^+$ patients were incubated in the presence of immobilized CD3 mAb (5 µg/ml) and CD39 mAb (upper histogram) or in the presence of autologous CD4$^+$CD25$^{high}$ Tregs (4:1 ratio CD8:Tregs) (middle histogram) or in the presence of autologous CD4$^+$CD25$^{high}$ Treg pre-incubated with CD39 mAb (bottom histogram). After 72 h, percentages of divided cells (CFSE low) were determined by flow cytometry. B. Percentages of inhibition of CD8 T cell proliferation in the presence of autologous CD4$^+$CD25$^{high}$ cells (upper panel) are calculated as (% of CFSE$^{low}$ CD8$^+$ T cells in the presence of autologous CD4$^+$CD25$^{high}$ cells)×100 (% Of CFSE$^{low}$ CD8$^+$ T cells in the absence of CD4$^+$CD25$^{high}$ cells). Percentages of restoration of CD8 T cell proliferation in the presence of anti-CD39 mAb (lower panel) are calculated as 100−(% CFSE$^{low}$ CD8$^+$ T cells in the presence of autologous CD4$^+$CD25$^{high}$ cells pre-treated with CD39)×100/(% CFSE$^{low}$ in the presence of autologous CD4$^+$CD25$^{high}$ cells). p values assessed by Wilcoxon's and Man-Witney's non-parametric tests are indicated.

Figure 3:
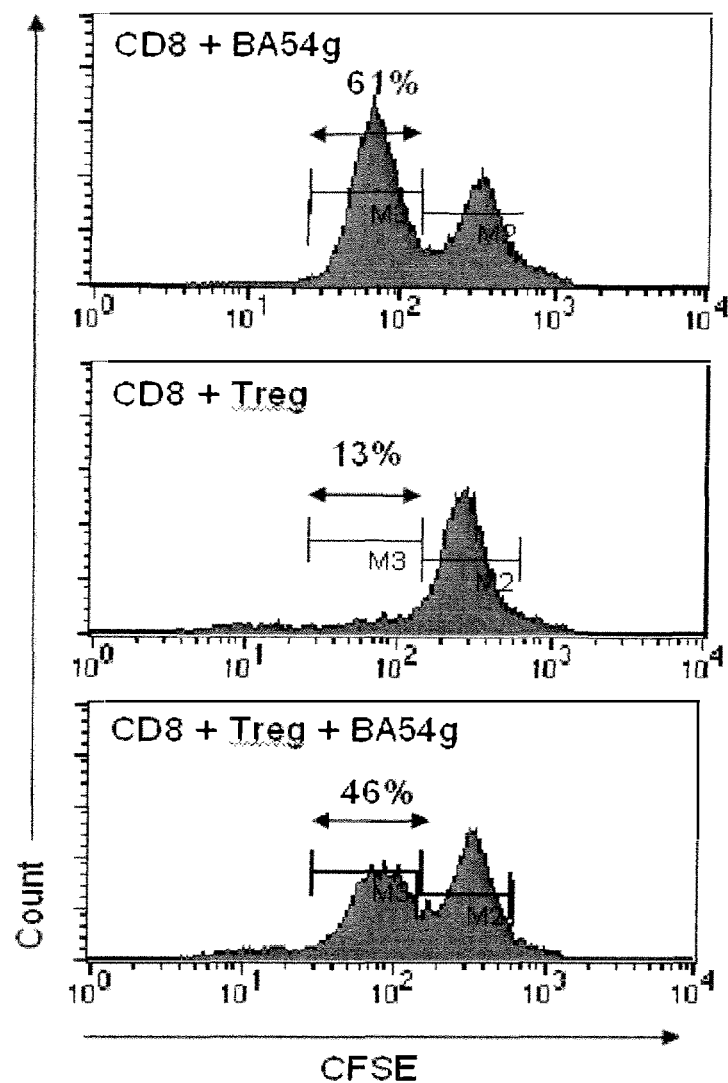

FIG. 3: Effect of the CD39 mAb, BA54g, on the immunosuppressive activity of CD4$^+$CD25$^{high}$ regulatory T cells. A. CFSE-labeled CD8 T cells from HIV$^+$ patients were incubated in the presence of immobilized CD3 mAb (5 µg/ml) and BA54g mAb (upper histogram) or in the presence of autologous CD4$^+$CD25$^{high}$ Tregs (4:1 ratio CD8: Tregs) (middle histogram) or in the presence of autologous CD4$^+$CD25$^{high}$ Treg pre-incubated with BA54g mAb (bottom histogram). After 72 h, percentages of divided cells (CFSE low) were determined by flow cytometry.

Figure 4:
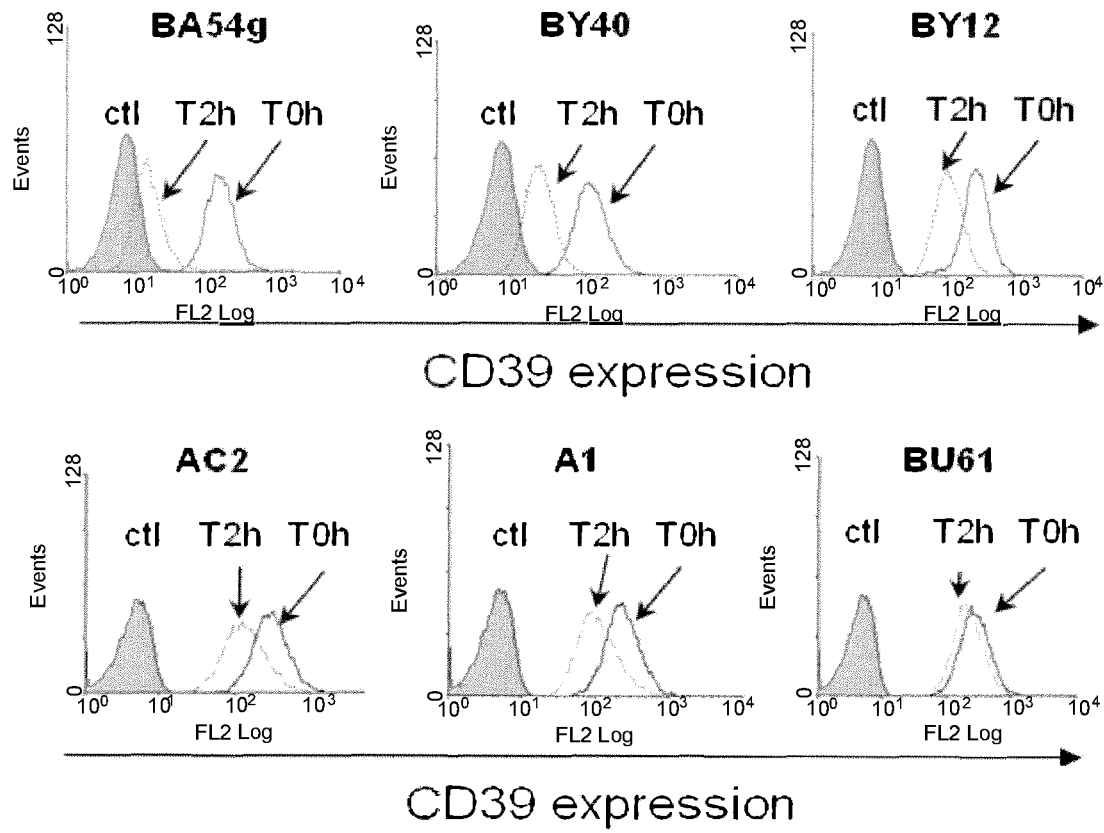

FIG. 4: Modulation of CD39 expression by several anti-CD39 mAbs. YT2C2 NK cells (1×10$^6$ cells/ml) were cultured in a 96 wells plate in presence of BY12, BY40, BA54g, A1 (Biolegend), BU61 (Santa Cruz Biotech) or AC2 (Immunotech) (10 µg/ml) for 2 h at 37° C. Then cells were washed and incubated for 20 min at 4° C. with the same antibody (10 µg/ml) that had been used for the culture. Antibody fixation was revealed with APC-coupled goat anti-mouse Ab and measured by flow cytometry. Percentage of inhibition of antibody fixation was calculated according to the following formula: 100−(MFI of mAb-treated cells/ MFI of control isotype-treated cells)*100.

EXAMPLE

Expression of CD39 on CD4+CD25low and CD4+CD25high T cells from HIV− controls and HIV+ patients: It has been recently reported that mouse and human CD4+CD25high regulatory T cells constitutively express CD39, an ectonucleotidase that converts extra-cellular ATP generated in sites of immune activation, leading to adenosine generation an inhibitor of cell proliferation, Here we used the anti-CD39 mAb BY40 to examine the expression of CD39 on CD4+CD25low and CD4+CD25high peripheral blood lymphocyte (PBL) populations from both HIV− controls and HIV+ patients. Results from FIG. 1, indicate that the percentage of CD39+ cells within CD4+CD25high subpopulation is significantly higher (p<0.01) than the percentage of CD39+ cells within CD4+CD25low subpopulation in PBL from both HIV− and HIV+ individuals (FIG. 1A). Means are 16% versus 46% (HIV−) and 17% versus 42% (HIV+). No statistical differences were observed between the percentage of CD39+ cells when compare each of the same CD4+ the population between HIV− and HIV+ groups.

Next we analyzed the level of expression of CD39 on CD4+ cells from both HIV+ and HIV− individual (FIGS. 1B and 1C). We observed that CD39 expression on CD4+CD25low and CD4+CD25high of HIV+ patients is significantly higher as compared to the level of CD39 expression on cells of HIV− controls (means 84 versus 45 and 136 versus 93 respectively).

These results indicate that a higher percentage of CD4+CD25high stained positive for CD39 as compared to CD4+CD25low population and that both CD4+CD25high and CD4+CD25low regulatory T cells from HIV+ patients expressed a higher level of CD39.

Blocking CD39 on CD4+CD25high regulatory T cells reverts their immunosuppressive effect towards autologous CD8 effector T cells: Having demonstrated that CD4+CD25high regulatory T cells from HIV+ patients expressed a high level of CD39, we examined the possible role of CD39 in HIV+ regulatory T cells-mediated inhibition of CD8 T cell proliferation.

As expected we observed, in co-cultures experiments, that autologous untreated CD4+CD25high regulatory T cells efficiently inhibit CD8+ T cell proliferation, an effect that is not observed when CD4+CD25high regulatory T cells have previously been incubated in the presence of the CD39 mAb BY40 (FIG. 2A, bottom histogram). The CD39 mAb has no direct effect on proliferation of CD8+ T cells (FIG. 2A, upper histogram). The capacity of BY40 mAb to reverse immunosuppressive effect of CD4+CD25high regulatory T cells, is not limited to CD4+CD25high regulatory T cells from HIV+ patients. A similar effect has been observed in co-culture experiments done with T cells from HIV− individuals. However BY40 mAb was more efficient to inhibit immunosuppressive activity of CD4+CD25high regulatory T cells and to restore proliferation of autologous CD8 T cells from HIV+ patients (FIG. 2B).

These results indicate that triggering of CD39 molecule on CD4+CD25high regulatory T cells with BY40 mAb can revert their immunosuppressive activity and restore proliferation of autologuous CD8 T cells induced by CD3 mAb.

The effect observed with the BY40 mAb has been extended to another anti-CD39, the BA54g mAb (FIG. 3).

Down-regulation of CD39 molecule induced by CD39 mAbs. As a potential mechanism of action for BY40 and BA54g mAbs, we measured their capacity to down-modulate the expression of CD39 on cell surface. As shown in FIG. 4, we demonstrated that incubation of YT2C2 cells for 2 h in the presence of BA54g or BY40 mAb led to a potent inhibition of CD39 expression (>70% of inhibition). We did not observed significant modulation of CD39 expression with BU61 mAb, whereas BY12, A1 and AC2 mAb induced an intermediate down-modulation of CD39 cell surface expression.

Pre-treatment of CD4+CD25high regulatory T cells with BY40 mAb partially reverts their immunosuppressive effect towards the generation of tumor-specific cytotoxic effector CD4 T cells. We next measured the capacity of the BY40 mAb to sustained generation of tumor-specific T cells with effector functions. As demonstrated in Table 3, co-culture of PBL with CD4+CD25high Tregs and the melanoma cell line HM11 led to the generation of low level of cytotoxic effector CD4 T cells as revealed by the acquisition of the CD107 expression, a degranulation specific marker. Preliminary experiments showed that pre-treatment of CD4+CD25high Tregs with the BY40 mAb slightly increased percentage CD4+CD107+ effector T cells (Table 3), suggesting that BY40 mAb partially reverts Tregs immunosuppressive activity and enables generation of cytotoxic T cells.

TABLE 3

Effect of the CD39 mAb, BY40, on the generation of tumor-specific cytotoxic CD4 T cells.

|  | % expression CD107a | increase CTL activity % |
|---|---|---|
| CD4 + CD25high + IgG1 | 4.21% |  |
| CD4 + CD25high + BY40 | 6.56% | 56% |

$2 \times 10^5$ peripheral blood mononuclear cells and $1 \times 10^5$ HM11 irradiated tumor cells (60 Gray) supplemented with $5 \times 10^4$ purified $CD4^+CD25^{high}$ cells (Treg), that have been previously incubated for 1 h with either IgG1 control or BY40 mAb (10 µg/ml) were co-cultured for 6 days. Every 48 h, 0.5 µg of IgG1 control or BY40 mAb were added to the culture. Then lymphocytes were harvested and incubated in a 96 wells plate with HM11 cells (1/1 ratio) in the presence of either IgG1 control or BY40 mAb (10 µg/ml). Percentage of tumor-specific effector cytotoxic CD4 T cells was determined by labeling with anti-CD107a-PC5 antibody in the presence of Monensin (2 µM final concentration). After 4 h at 37° C. 5% C02, cells were washed and stained with anti-CD4-FITC antibody. The dual expression of CD4 and CD107a was measured by flow cytometry. The percentage of CD107a expression restoration was measured according to the following formula: (% of $CD4^+CD107a^+$ cells following BY40 treatment)–(% of $CD4^+CD107a^+$ cells following control IgG1 treatment)/% of $CD4^+CD107a^+$ cells following control IgG1 treatment)*100.

BA54g mAb inhibits ATPase activity of human PBMC. CD39 has been previously described as an integral component of the suppressive machinery of Tregs, acting at least in part through the modulation of pericellular levels of adenosine. We analyzed here the effect of BA54g CD39 mAb on the spontaneous ATPase activity of human PBMC. We observed that spontaneous ATPase activity of human PBMC following 24 h culture in the presence of BA54g was decreased by 29% compared to PBMC cultured in the presence of control IgG1 (Table 4). The effect of others CD39 mAb and in particular BY40 is currently under investigation.

TABLE 4

Effect of the CD39 mAb, BA54g, on ATPase activity of human peripheral blood mononuclear cells (PBMC).

|  | OD 620 nM | % inhibition |
|---|---|---|
| control IgG1 | 0.215 |  |
| BA54g | 0.151 | 29% |

$4 \times 10^5$ PBMC were cultured in complete RPMI medium in the presence of BA54g mAb or IgG1 control (10 µg/ml). After 24 h, cells were washed three times in phosphate-free buffer (10 mM glucose, 20 mM Hepes, 5 mM KCL, 120 mM NaCl, 2 mM CaCl2)) and resuspended in 400 µl of incubation buffer supplemented with 2 mM ATP. After 10 min at 37° C. cells were centrifuged, phosphate concentration in the supernatants was measured by spectrophotometer (620 nM) after addition of Malachite green/polyvinylalcohol/ammonium molybate solution for 20 min.

REFERENCES

Bluestone, J. A. & Abbas, A. K. Natural versus adaptive regulatory T cells. Nature Rev. Immunol. 3, 253-257 (2003).
Brady G, Jantzen H M, Bernard H U, Brown R, Schutz G, Hashimoto-Gotoh T. New cosmid vectors developed for eukaryotic DNA cloning. Gene. 1984 February; 27(2): 223-32.
Caron P C, Laird W, Co M S, Avdalovic N M, Queen C, Scheinberg D A. Engineered humanized dimeric forms of IgG are more effective antibodies. J Exp Med. 1992 Oct. 1; 176(4):1191-5.
Chardes T, Villard S, Ferrieres G, Piechaczyk M, Cerutti M, Devauchelle G Pau B. Efficient amplification and direct sequencing of mouse variable regions from any immunoglobulin gene family. FEBS Lett. 1999 Jun. 11; 452 (3):386-94.
Cole et al. "Monoclonal Antibodies and Cancer Therapy", Alan R. Liss, Inc., 1985, pp. 77-96.
Connolly D C, Bao R, Nikitin A Y, Stephens K C, Poole T W, Hua X, Harris S S, Vanderhyden B C, Hamilton T C. Female mice chimeric for expression of the simian virus 40 TAg under control of the MISIIR promoter develop epithelial ovarian cancer. Cancer Res. 2003 Mar. 15; 63(6):1389-97.
Cote R J, Morrissey D M, Houghton A N, Beattie E J Jr, Oettgen H F, Old L J. "Generation of human monoclonal antibodies reactive with cellular antigens". Proc Natl Acad Sci USA. 1983 April; 80(7):2026-30.
Deaglio S, Dwyer K M, Gao W, Friedman D, Usheva A, Erat A, Chen J F, Enjyoji K, Linden J, Oukka M, Kuchroo V K, Strom T B, Robson S C. Adenosine generation catalyzed by CD39 and CD73 expressed on regulatory T cells mediates immune suppression. J Exp Med. 2007 Jun. 11; 204(6):1257-65. Epub 2007 May 14.
Edge A S, Faltynek C R, Hof L, Reichert L E Jr, Weber P. Deglycosylation of glycoproteins by trifluoromethanesulfonic acid. Anal Biochem. 1981 Nov. 15; 118(1):131-7.
Gazzano-Santoro H, Ralph P, Ryskamp T C, Chen A B, Mukku V R. A non-radioactive complement-dependent cytotoxicity assay for anti-CD20 monoclonal antibody. J Immunol Methods. 1997 Mar. 28; 202(2):163-71.
Gillies S D, Morrison S L, Oi V T, Tonegawa S. A tissue-specific transcription enhancer element is located in the major intron of a rearranged immunoglobulin heavy chain gene. Cell. 1983 July; 33(3):717-28.
Köhler G., M. C. (1975) Nature 256, 495-497.
Kuwana Y, Asakura Y, Utsunomiya N, Nakanishi M, Arata Y, Itoh S, Nagase F, Kurosawa Y. Expression of chimeric receptor composed of immunoglobulin-derived V regions and T-cell receptor-derived C regions. Biochem Biophys Res Commun. 1987 Dec. 31; 149(3):960-8.
Mason J O, Williams G T, Neuberger M S. Transcription cell type specificity is conferred by an immunoglobulin VH gene promoter that includes a functional consensus sequence. Cell. 1985 June; 41(2):479-87.
Miyaji H, Mizukami T, Hosoi S, Sato S, Fujiyoshi N, Itoh S. Expression of human beta-interferon in Namalwa KJM-1 which was adapted to serum-free medium. Cytotechnology. 1990 March; 3(2):133-40.
Mizukami T, Itoh S. A new SV40-based vector developed for cDNA expression in animal cells. J Biochem (Tokyo). 1987 May; 101(5):1307-10.

Morrison S L, Johnson M J, Herzenberg L A, Oi V T. Chimeric human antibody molecules: mouse antigen-binding domains with human constant region domains. Proc Natl Acad Sci USA. 1984 November; 81(21):6851-5.

Neuberger M S, Williams G T, Fox R O. Recombinant antibodies possessing novel effector functions. Nature. 1984 Dec. 13-19; 312(5995):604-8.

O'Hare K, Benoist C, Breathnach R. Transformation of mouse fibroblasts to methotrexate resistance by a recombinant plasmid expressing a prokaryotic dihydrofolate reductase. Proc Natl Acad Sci USA. 1981 March; 78(3):1527-31.

Padlan E A. A possible procedure for reducing the immunogenicity of antibody variable domains while preserving their ligand-binding properties. Mol Immunol. 1991 April-May; 28(4-5):489-98.

Riechmann L, Clark M, Waldmann H, Winter G Reshaping human antibodies for therapy. Nature. 1988 Mar. 24; 332(6162):323-7.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994 Feb. 1; 91(3):969-73.

Shitara K, Nakamura K, Tokutake-Tanaka Y, Fukushima M, Hanai N. A new vector for the high level expression of chimeric antibodies in myeloma cells. J Immunol Methods. 1994 Jan. 3; 167(1-2):271-8.

Shopes B. A genetically engineered human IgG mutant with enhanced cytolytic activity. J Immunol. 1992 May 1; 148(9):2918-22.

Strohal R, Kroemer G, Wick G, Kofler R. Complete variable region sequence of a nonfunctionally rearranged kappa light chain transcribed in the nonsecretor P3-X63-Ag8.653 myeloma cell line. Nucleic Acids Res. 1987 Mar. 25; 15(6):2771.

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994 June; 7(6):805-14.

Thotakura N R, Bahl O P. Enzymatic deglycosylation of glycoproteins. Methods Enzymol. 1987; 138:350-9.

Urlaub G, Chasin L A. Isolation of Chinese hamster cell mutants deficient in dihydrofolate reductase activity. Proc Natl Acad Sci USA. 1980 July; 77(7):4216-20.

The invention claimed is:

1. An anti-CD39 antibody or antigen binding fragment thereof comprising:
   a heavy chain wherein the variable domain comprises the sequence of SEQ ID NO:2 for CDR-H1, SEQ ID NO:3 for CDR-H2 and SEQ ID NO:4 for CDR-H3; and
   a light chain wherein the variable domain comprises the sequence of SEQ ID NO:6 for CDR-L1, SEQ ID NO:7 for CDR-L2 and SEQ ID NO:8 for CDR-L3.

2. The anti-CD39 antibody or antigen binding fragment thereof of claim 1, which comprises:
   a heavy chain variable region having the amino acid sequence set forth as SEQ ID NO: 1 and
   a light chain variable region having the amino acid sequence set forth as SEQ ID NO: 5.

3. The anti-CD39 antibody or antigen binding fragment thereof of claim 1, wherein said anti-CD39 antibody or antigen binding fragment thereof is selected from the group consisting of a Fv, Fab, F(ab')2, Fab', dsFv, scFv, sc(Fv)2, a diabody, and multispecific antibodies formed from antibody fragments.

4. The anti-CD39 antibody or antigen binding fragment thereof according to claim 3 that is a humanized antibody or antigen binding fragment.

5. A pharmaceutical composition comprising the anti-CD39 antibody or antigen binding fragment thereof according to any one of claims 1, 2, and 3-4 and a pharmaceutically acceptable carrier.

6. The pharmaceutical composition of claim 5, wherein the pharmaceutical composition comprises a therapeutically effective amount of the antibody or antigen binding fragment thereof for treating cancer or an infectious disease associated with an increased T regulatory cell (Treg) activity.

7. The pharmaceutical composition of claim 6, wherein the cancer is selected from the group consisting in lung cancer, breast cancer, ovarian cancer, melanoma, liver cancer, gastric cancer and lymphoma.

8. A method of treating a subject for a cancer or an infectious disease associated with an increased T regulatory cell (Treg) activity comprising administering the pharmaceutical composition of claim 6 to a subject in need of treatment for a cancer or an infectious disease associated with an increased T regulatory cell (Treg) activity.

9. The method of claim 8, wherein the cancer is selected from the group consisting in lung cancer, breast cancer, ovarian cancer, melanoma, liver cancer, gastric cancer and lymphoma.

* * * * *

SEQUENCE LISTING

```
<160> NUMBER OF SEQ ID NOS: 38

<210> SEQ ID NO 1
<211> LENGTH: 187
<212> TYPE: PRT
<213> ORGANISM: Mus musculus

<400> SEQUENCE: 1

Thr Arg Val Lys Lys Pro Arg Glu Thr Val Lys Ile Ser Cys Lys Ala
1               5                   10                  15

Ser Gly Tyr Thr Phe Thr His Tyr Gly Met Asn Trp Val Lys Gln Ala
            20                  25                  30

Pro Gly Lys Gly Leu Lys Trp Met Gly Trp Ile Asn Thr Tyr Thr Gly
        35                  40                  45

Glu Pro Thr Tyr Ala Asp Asp Phe Lys Gly Arg Phe Ala Phe Ser Leu
    50                  55                  60

Glu Ala Ser Val Ser Thr Ala Tyr Leu Gln Ile Asn Asn Leu Lys Asn
65                  70                  75                  80

Glu Asp Thr Ala Thr Tyr Phe Cys Ala Arg Arg Arg Tyr Glu Gly Asn
                85                  90                  95

Tyr Val Phe Tyr Tyr Phe Asp Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Gln Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser
            180                 185

<210> SEQ ID NO 2
```

```
<211> LENGTH: 8
<212> TYPE: PRT
<213> ORGANISM: Mus musculus

<400> SEQUENCE: 2

Gly Tyr Thr Phe Thr His Tyr Gly
1               5

<210> SEQ ID NO 3
<211> LENGTH: 8
<212> TYPE: PRT
<213> ORGANISM: Mus musculus

<400> SEQUENCE: 3

Ile Asn Thr Tyr Thr Gly Glu Pro
1               5

<210> SEQ ID NO 4
<211> LENGTH: 27
<212> TYPE: PRT
<213> ORGANISM: Mus musculus

<400> SEQUENCE: 4

Ala Arg Arg Arg Tyr Glu Gly Asn Tyr Val Phe Tyr Tyr Phe Asp Tyr
1               5                   10                  15

Trp Gly Gln Gly Thr Thr Leu Thr Val Ser Ser
            20                  25

<210> SEQ ID NO 5
<211> LENGTH: 165
<212> TYPE: PRT
<213> ORGANISM: Mus musculus

<400> SEQUENCE: 5

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Phe Ser Trp Tyr Gln Gln Lys Gln Gly Lys Ser Pro Gln Leu Leu Val
        35                  40                  45

Tyr Thr Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Val Thr Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp
                165

<210> SEQ ID NO 6
<211> LENGTH: 11
<212> TYPE: PRT
```

-continued

<213> ORGANISM: Mus musculus

<400> SEQUENCE: 6

Arg Ala Ser Glu Asn Ile Tyr Ser Tyr Phe Ser
1               5                   10

<210> SEQ ID NO 7
<211> LENGTH: 7
<212> TYPE: PRT
<213> ORGANISM: Mus musculus

<400> SEQUENCE: 7

Thr Ala Lys Thr Leu Ala Glu
1               5

<210> SEQ ID NO 8
<211> LENGTH: 20
<212> TYPE: PRT
<213> ORGANISM: Mus musculus

<400> SEQUENCE: 8

Gln His His Tyr Val Thr Pro Tyr Thr Phe Gly Gly Gly Thr Lys Leu
1               5                   10                  15

Glu Ile Lys Arg
            20

<210> SEQ ID NO 9
<211> LENGTH: 345
<212> TYPE: DNA
<213> ORGANISM: Artificial Sequence
<220> FEATURE:
<223> OTHER INFORMATION: cDNA

<400> SEQUENCE: 9
acgcgagtga agaagcctcg agagacagtc aagatctcct gcaaggcttc tgggtatacc      60
ttcacacact atggaatgaa ctgggtgaag caggctccag aaagggtttt aaagtggatg     120
ggctggataa acacctacac tggagagcca acatatgctg atgacttcaa gggacggttt     180
gccttctctt tggaagcctc tgtcagcact gcctatttgc agatcaacaa cctcaaaaat     240
gaggacacgg ctacatattt ctgtgcaaga aggagatatg agggtaacta cgttttttac     300
tactttgact actggggcca aggcaccact ctcacagtct cctca                     345

<210> SEQ ID NO 10
<211> LENGTH: 324
<212> TYPE: DNA
<213> ORGANISM: Artificial Sequence
<220> FEATURE:
<223> OTHER INFORMATION: cDNA

<400> SEQUENCE: 10
gacatccaga tgactcagtc tccagcctcc ctatctgcat ctgtgggaga aactgtcacc      60
atcacatgtc gagcaagtga aaatatttac agttattttt catggtatca gcagaaacag     120
ggaaaatctc ctcagctcct ggtctatact gcaaaaacct agcagaagg tgtgccatca      180
aggttcagtg gcagtggatc aggcacacag ttttctctga agatcaacag cctgcagcct     240
gaagattttg ggagttatta ctgtcaacat cattatgtta ctccgtacac gttcggaggg     300
gggaccaagc tggaaataaa acgg                                            324

<210> SEQ ID NO 11
<211> LENGTH: 118

<212> TYPE: PRT
<213> ORGANISM: Mus musculus
<220> FEATURE:
<221> NAME/KEY: VARIANT
<222> LOCATION: (0)...(0)
<223> OTHER INFORMATION: BA54g

<400> SEQUENCE: 11

Asp Val Gln Leu Val Glu Ser Gly Gly Gly Leu Val Gln Pro Gly Gly
1               5                   10                  15
Ser Arg Lys Leu Ser Cys Ala Ala Ser Gly Phe Thr Phe Ser Ser Phe
                20                  25                  30
Gly Met His Trp Val Arg Gln Ala Pro Glu Lys Gly Leu Glu Trp Val
            35                  40                  45
Ala Tyr Ile Ser Ser Gly Ser Ser Ile Ile Tyr Tyr Ala Asp Thr Val
        50                  55                  60
Lys Gly Arg Phe Thr Ile Ser Arg Asp Asn Pro Lys Asn Thr Leu Phe
65                  70                  75                  80
Leu Gln Met Thr Ser Leu Gly Ser Glu Asp Thr Ala Met Tyr Tyr Cys
                85                  90                  95
Ala Arg Trp Ser Thr Thr Val Val Ala Thr Asp Tyr Trp Gly Gln Gly
            100                 105                 110
Thr Thr Leu Thr Val Ser
        115

<210> SEQ ID NO 12
<211> LENGTH: 21
<212> TYPE: PRT
<213> ORGANISM: Mus musculus
<220> FEATURE:
<221> NAME/KEY: VARIANT
<222> LOCATION: (0)...(0)
<223> OTHER INFORMATION: BA54g

<400> SEQUENCE: 12

Gly Gly Ser Arg Lys Leu Ser Cys Ala Ala Ser Gly Phe Thr Phe Ser
1               5                   10                  15
Ser Phe Gly Met His
            20

<210> SEQ ID NO 13
<211> LENGTH: 17
<212> TYPE: PRT
<213> ORGANISM: Mus musculus
<220> FEATURE:
<221> NAME/KEY: VARIANT
<222> LOCATION: (0)...(0)
<223> OTHER INFORMATION: BA54g

<400> SEQUENCE: 13

Tyr Ile Ser Ser Gly Ser Ser Ile Ile Tyr Tyr Ala Asp Thr Val Lys
1               5                   10                  15
Gly

<210> SEQ ID NO 14
<211> LENGTH: 20
<212> TYPE: PRT
<213> ORGANISM: Mus musculus
<220> FEATURE:
<221> NAME/KEY: VARIANT
<222> LOCATION: (0)...(0)
<223> OTHER INFORMATION: BA54g

<400> SEQUENCE: 14

```
Trp Ser Thr Thr Val Ala Thr Asp Tyr Trp Gly Gln Gly Thr Thr
1               5                   10                  15

Leu Thr Val Ser
            20

<210> SEQ ID NO 15
<211> LENGTH: 108
<212> TYPE: PRT
<213> ORGANISM: Mus musculus
<220> FEATURE:
<221> NAME/KEY: VARIANT
<222> LOCATION: (0)...(0)
<223> OTHER INFORMATION: BA54g

<400> SEQUENCE: 15

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
                20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Gly Tyr Ser Tyr Pro Tyr
                85                  90                  95

Thr Phe Gly Gly Gly Thr Lys Leu Glu Ile Lys Arg
            100                 105

<210> SEQ ID NO 16
<211> LENGTH: 11
<212> TYPE: PRT
<213> ORGANISM: Mus musculus
<220> FEATURE:
<221> NAME/KEY: VARIANT
<222> LOCATION: (0)...(0)
<223> OTHER INFORMATION: BA54g

<400> SEQUENCE: 16

Lys Ala Ser Glu Asn Val Val Thr Tyr Val Ser
1               5                   10

<210> SEQ ID NO 17
<211> LENGTH: 7
<212> TYPE: PRT
<213> ORGANISM: Mus musculus
<220> FEATURE:
<221> NAME/KEY: VARIANT
<222> LOCATION: (0)...(0)
<223> OTHER INFORMATION: BA54g

<400> SEQUENCE: 17

Gly Ala Ser Asn Arg Tyr Thr
1               5

<210> SEQ ID NO 18
<211> LENGTH: 21
<212> TYPE: PRT
<213> ORGANISM: Mus musculus
<220> FEATURE:
<221> NAME/KEY: VARIANT
<222> LOCATION: (0)...(0)
<223> OTHER INFORMATION: BA54g
```

-continued

<400> SEQUENCE: 18

Cys Gly Gln Gly Tyr Ser Tyr Pro Tyr Thr Phe Gly Gly Gly Thr Lys
1               5                   10                  15

Leu Glu Ile Lys Arg
            20

<210> SEQ ID NO 19
<211> LENGTH: 5
<212> TYPE: PRT
<213> ORGANISM: Artificial Sequence
<220> FEATURE:
<223> OTHER INFORMATION: BY12

<400> SEQUENCE: 19

Asn Tyr Gly Met Asn
1               5

<210> SEQ ID NO 20
<211> LENGTH: 17
<212> TYPE: PRT
<213> ORGANISM: Artificial Sequence
<220> FEATURE:
<223> OTHER INFORMATION: BY12

<400> SEQUENCE: 20

Trp Ile Asn Thr Tyr Thr Gly Glu Pro Thr Tyr Ala Asp Asp Phe Lys
1               5                   10                  15

Gly

<210> SEQ ID NO 21
<211> LENGTH: 12
<212> TYPE: PRT
<213> ORGANISM: Artificial Sequence
<220> FEATURE:
<223> OTHER INFORMATION: BY12

<400> SEQUENCE: 21

Lys Ala Tyr Tyr Gly Ser Asn Tyr Tyr Phe Asp Tyr
1               5                   10

<210> SEQ ID NO 22
<211> LENGTH: 7
<212> TYPE: PRT
<213> ORGANISM: Artificial Sequence
<220> FEATURE:
<223> OTHER INFORMATION: BY12

<400> SEQUENCE: 22

Gly Tyr Thr Phe Arg Asn Tyr
1               5

<210> SEQ ID NO 23
<211> LENGTH: 4
<212> TYPE: PRT
<213> ORGANISM: Artificial Sequence
<220> FEATURE:
<223> OTHER INFORMATION: BY12

<400> SEQUENCE: 23

Thr Tyr Thr Gly
1

<210> SEQ ID NO 24
<211> LENGTH: 10

-continued

```
<212> TYPE: PRT
<213> ORGANISM: Artificial Sequence
<220> FEATURE:
<223> OTHER INFORMATION: BY12

<400> SEQUENCE: 24

Ala Tyr Tyr Gly Ser Asn Tyr Tyr Phe Asp
1               5                   10

<210> SEQ ID NO 25
<211> LENGTH: 8
<212> TYPE: PRT
<213> ORGANISM: Artificial Sequence
<220> FEATURE:
<223> OTHER INFORMATION: BY12

<400> SEQUENCE: 25

Gly Tyr Thr Phe Arg Asn Tyr Gly
1               5

<210> SEQ ID NO 26
<211> LENGTH: 8
<212> TYPE: PRT
<213> ORGANISM: Artificial Sequence
<220> FEATURE:
<223> OTHER INFORMATION: BY12

<400> SEQUENCE: 26

Ile Asn Thr Tyr Thr Gly Glu Pro
1               5

<210> SEQ ID NO 27
<211> LENGTH: 14
<212> TYPE: PRT
<213> ORGANISM: Artificial Sequence
<220> FEATURE:
<223> OTHER INFORMATION: BY12

<400> SEQUENCE: 27

Ala Arg Lys Ala Tyr Tyr Gly Ser Asn Tyr Tyr Phe Asp Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: BY12

<400> SEQUENCE: 28

Lys Ala Ser Gln Asp Val Ser Thr Ala Val Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: BY12

<400> SEQUENCE: 29

Ser Ala Ser Tyr Arg Tyr Thr
1               5

<210> SEQ ID NO 30
<211> LENGTH: 10
<212> TYPE: PRT
```

```
<213> ORGANISM: Artificial Sequence
<220> FEATURE:
<223> OTHER INFORMATION: BY12

<400> SEQUENCE: 30

Gln Gln His Tyr Thr Thr Pro Pro Tyr Thr
1               5                   10

<210> SEQ ID NO 31
<211> LENGTH: 7
<212> TYPE: PRT
<213> ORGANISM: Artificial Sequence
<220> FEATURE:
<223> OTHER INFORMATION: BY12

<400> SEQUENCE: 31

Ser Gln Asp Val Ser Thr Ala
1               5

<210> SEQ ID NO 32
<211> LENGTH: 3
<212> TYPE: PRT
<213> ORGANISM: Artificial Sequence
<220> FEATURE:
<223> OTHER INFORMATION: BY12

<400> SEQUENCE: 32

Ser Ala Ser
1

<210> SEQ ID NO 33
<211> LENGTH: 7
<212> TYPE: PRT
<213> ORGANISM: Artificial Sequence
<220> FEATURE:
<223> OTHER INFORMATION: BY12

<400> SEQUENCE: 33

His Tyr Thr Thr Pro Pro Tyr
1               5

<210> SEQ ID NO 34
<211> LENGTH: 6
<212> TYPE: PRT
<213> ORGANISM: Artificial Sequence
<220> FEATURE:
<223> OTHER INFORMATION: BY12

<400> SEQUENCE: 34

Gln Asp Val Ser Thr Ala
1               5

<210> SEQ ID NO 35

<400> SEQUENCE: 35

000

<210> SEQ ID NO 36
<211> LENGTH: 10
<212> TYPE: PRT
<213> ORGANISM: Artificial Sequence
<220> FEATURE:
<223> OTHER INFORMATION: BY12

<400> SEQUENCE: 36

Gln Gln His Tyr Thr Thr Pro Pro Tyr Thr
```

-continued

```
1               5                   10
```

<210> SEQ ID NO 37
<211> LENGTH: 108
<212> TYPE: PRT
<213> ORGANISM: Artificial Sequence
<220> FEATURE:
<223> OTHER INFORMATION: BY12

<400> SEQUENCE: 37

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Thr Val Gln Ala
65                  70                  75                  80

Glu Asp Leu Ala Val Tyr Tyr Cys Gln Gln His Tyr Thr Thr Pro Pro
                85                  90                  95

Tyr Thr Phe Gly Gly Gly Thr Lys Leu Glu Ile Lys
            100                 105
```

<210> SEQ ID NO 38
<211> LENGTH: 121
<212> TYPE: PRT
<213> ORGANISM: Artificial Sequence
<220> FEATURE:
<223> OTHER INFORMATION: BY12

<400> SEQUENCE: 38

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Arg Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Ala Thr Ser Ala Ser Thr Ala Tyr
65                  70                  75                  80

Leu Gln Ile Ser Asn Leu Lys Asn Glu Asp Thr Ala Thr Tyr Phe Cys
                85                  90                  95

Ala Arg Lys Ala Tyr Tyr Gly Ser Asn Tyr Tyr Phe Asp Tyr Trp Gly
            100                 105                 110

Gln Gly Thr Thr Leu Thr Val Ser Ser
        115                 120
```